United States Patent
Wulhfard

(10) Patent No.: US 9,580,485 B2
(45) Date of Patent: Feb. 28, 2017

(54) IL-12 IMMUNOCONJUGATE

(75) Inventor: Sarah Wulhfard, Baden (CH)

(73) Assignee: Philogen S.p.A., Siena (IT)

(*) Notice: Subject to any disclaimer, the term of this patent is extended or adjusted under 35 U.S.C. 154(b) by 237 days.

(21) Appl. No.: 14/234,081

(22) PCT Filed: Jul. 24, 2012

(86) PCT No.: PCT/EP2012/064490
§ 371 (c)(1),
(2), (4) Date: Jan. 21, 2014

(87) PCT Pub. No.: WO2013/014149
PCT Pub. Date: Jan. 31, 2013

(65) Prior Publication Data
US 2014/0170109 A1 Jun. 19, 2014

Related U.S. Application Data

(60) Provisional application No. 61/512,190, filed on Jul. 27, 2011.

(51) Int. Cl.
C07K 14/54 (2006.01)
A61K 47/48 (2006.01)
C07K 16/18 (2006.01)

(52) U.S. Cl.
CPC .... *C07K 14/5434* (2013.01); *A61K 47/48423* (2013.01); *A61K 47/48538* (2013.01); *C07K 16/18* (2013.01)

(58) Field of Classification Search
CPC ..... C07K 16/00; C07K 16/28; C07K 14/5434
See application file for complete search history.

(56) References Cited

U.S. PATENT DOCUMENTS

| | | | | |
|---|---|---|---|---|
| 8,222,377 B2* | 7/2012 | Kaspar | ........... | A61K 47/48423 530/391.7 |
| 8,481,684 B2* | 7/2013 | Rybak | ............. | A61K 51/1018 530/387.1 |
| 2009/0068106 A1* | 3/2009 | Corti | ................. | C07K 14/78 424/9.1 |
| 2010/0183506 A1* | 7/2010 | Neri | ................. | C07K 16/18 424/1.49 |
| 2010/0260707 A1* | 10/2010 | Kaspar | ........... | A61K 47/48423 424/85.2 |

FOREIGN PATENT DOCUMENTS

| | | |
|---|---|---|
| WO | WO-2005/066348 A2 | 7/2005 |
| WO | WO-2006/119897 A2 | 11/2006 |
| WO | WO-2008/120101 A2 | 10/2008 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol., Jul. 5, 2002, 320(2):415-28.*
Paul, Fundamental Immunology, 3rd Edition, 1993, pp. 292-295.1.*
Rudikoff et al Single amino acid substitution altering antigen-binding specificity. Proc Natl Acad Sci U S A. Mar. 1982;79(6):1979-83.*
Dickerson et al. Enhancement of the Antiangiogenic Activity of Interleukin-12 by Peptide Targeted Delivery of the Cytokine to alphavbeta3 Integrin. Mol Cancer Res 2004;2(12):663-73.*
Carnemolla et al., "Enhancement of the antitumor properties of interleukin-2 by its targeted delivery to the tumor blood vessel extracellular matrix," Blood. 99(5):1659-65 (2002).
Gafner et al., "An engineered antibody-interleukin-12 fusion protein with enhanced tumor vascular targeting properties," Int J Cancer. 119(9):2205-12 (2006).
Halin et al., "Enhancement of the antitumor activity of interleukin-12 by targeted delivery to neovasculature," Nat Biotechnol. 20(3):264-9 (2002).
Kriegsmann et al., "Expression of fibronectin splice variants and oncofetal glycosylated fibronectin in the synovial membranes of patients with rheumatoid arthritis and osteoarthritis," Rheumatol Int. 24(1):25-33 (2004).
Mårlind et al., "Antibody-mediated delivery of interleukin-2 to the stroma of breast cancer strongly enhances the potency of chemotherapy," Clin Cancer Res. 14(20):6515-24 (2008).
Pasche et al., "Cloning and characterization of novel tumor-targeting immunocytokines based on murine IL7," J Biotechnol. 154(1):84-92 (2011).
Pasche et al., "Immunocytokines: a novel class of potent armed antibodies," Drug Discov Today. 17(11-12):583-90 (2012).
Pasche et al., "The antibody-based delivery of interleukin-12 to the tumor neovasculature eradicates murine models of cancer in combination with paclitaxel," Clin Cancer Res. 18(15):4092-103 (2012).
Sommavilla et al., "Expression, engineering and characterization of the tumor-targeting heterodimeric immunocytokine F8-IL12," Protein Eng Des Sel. 23(8):653-61 (2010).
Trachsel et al., "Antibody-mediated delivery of IL-10 inhibits the progression of established collagen-induced arthritis," Arthritis Res Ther. 9(1):R9 (2007) (9 pages).
International Preliminary Report on Patentability for International Patent Application No. PCT/EP2012/064490 dated Nov. 20, 2013 (12 pages).
International Search Report for International Patent Application No. PCT/EP2012/064490 mailed Oct. 11, 2012 (5 pages).

(Continued)

*Primary Examiner* — Prema Mertz
(74) *Attorney, Agent, or Firm* — Clark & Elbing LLP

(57) ABSTRACT

Conjugate comprising interleukin-12 (IL-12) and a single chain targeting portion comprising two antigen binding sites. The targeting portion may comprise an antibody fragment such as a single chain diabody. The conjugate may be a single chain fusion protein. Use of single chain bivalent IL-12 immunocytokine for targeting the extra-cellular matrix (ECM) of tissues, particularly tumour neovasculature antigens, for example fibronectin. Use for treating cancer or pathological angiogenesis in a patient.

18 Claims, 7 Drawing Sheets

(56) References Cited

OTHER PUBLICATIONS

Written Opinion of International Preliminary Examining Authority for International Patent Application No. PCT/EP2012/064490 mailed Jul. 4, 2013 (6 pages).
Kontermann et al. *Antibody Engineering* vol. 2. 227-228 (2010).
Kontermann et al., "Intracellular and cell surface displayed single-chain diabodies" J Immunol Methods. 226(1-2):179-88 (1999) (Abstract Only).
Nettelbeck et al., "Targeting of adenovirus to endothelial cells by a bispecific single-chain diabody directed against the adenovirus fiber knob domain and human endoglin (CD105)," Mol Ther. 3(6):882-91 (2001).

\* cited by examiner

IWELKKDVYVVELDWYPDAPGEMVVLTCDTPEEDGITWTLDQSSEVLGSGKTLTIQVKEFGDAGQYT
CHKGGEVLSHSLLLLHKKEDGIWSTDILKDQKEPKNKTFLRCEAKNYSGRFTCWWLTTISTDLTFSVK
SSRGSSDPQGVTCGAATLSAERVRGDNKEYEYSVECQEDSACPAAEESLPIEVMVDAVHKLKYENYT
SSFFIRDIIKPDPPKNLQLKPLKNSRQVEVSWEYPDTWSTPHSYFSLTFCVQVQGKSKREKKDRVFTD
KTSATVICRKNASISVRAQDRYYSSSWSEWASVPCSGGGGSGGGGSGGGGSRNLPVATPDPGMFP
CLHHSQNLLRAVSNMLQKARQTLEFYPCTSEEIDHEDITKDKTSTVEACLPLELTKNESCLNSRETSFI
TNGSCLASRKTSFMMALCLSSIYEDLKMYQVEFKTMNAKLLMDPKRQIFLDQNMLAVIDELMQALNFN
SETVPQKSSLEEPDFYKTKIKLCILLHAFRIRAVTIDRVMSYLNASGSADGGEVQLLESGGGLVQPGGS
LRLSCAASGFTFSLFTMSWVRQAPGKGLEWVSAISGSGGSTYYADSVKGRFTISRDNSKNTLYLQM
NSLRAEDTAVYYCAKSTHLYLFDYWGQGTLVTVSSGGSGGEIVLTQSPGTLSLSPGERATLSCRASQ
SVSMPFLAWYQQKPGQAPRLLIYGASSRATGIPDRFSGSGSGTDFTLTISRLEPEDFAVYYCQQMRG
RPPTFGQGTKVEIKSSSSGSSSSGSSSSGEVQLLESGGGLVQPGGSLRLSCAASGFTFSLFTMSWV
RQAPGKGLEWVSAISGSGGSTYYADSVKGRFTISRDNSKNTLYLQMNSLRAEDTAVYYCAKSTHLYL
FDYWGQGTLVTVSSGGSGGEIVLTQSPGTLSLSPGERATLSCRASQSVSMPFLAWYQQKPGQAPRL
LIYGASSRATGIPDRFSGSGSGTDFTLTISRLEPEDFAVYYCQQMRGRPPTFGQGTKVEIK (SEQ ID
NO: 8)

CDR1 VH - LFT (SEQ ID NO: 9)
CDR2 VH - AISGS (SEQ ID NO: 10)
CDR3 VH - STHLYL (SEQ ID NO: 11)
CDR1 VL - MPF (SEQ ID NO: 12)
CDR2 VL - GASSRAT (SEQ ID NO: 13)
CDR3 VL - MRGRPP (SEQ ID NO: 14)

F8 VH –
EVQLLESGGGLVQPGGSLRLSCAASGFTFSLFTMSWVRQAPGKGLEWVSAISGSGGSTYYADSVKG
RFTISRDNSKNTLYLQMNSLRAEDTAVYYCAKSTHLYLFDYWGQGTLVTVSS (SEQ ID NO: 15)

F8 VL –
EIVLTQSPGTLSLSPGERATLSCRASQSVSMPFLAWYQQKPGQAPRLLIYGASSRATGIPDRFSGSGS
GTDFTLTISRLEPEDFAVYYCQQMRGRPPTFGQGTKVEIK (SEQ ID NO: 16)

p40
IWELKKDVYVVELDWYPDAPGEMVVLTCDTPEEDGITWTLDQSSEVLGSGKTLTIQVKEFGDAGQYT
CHKGGEVLSHSLLLLHKKEDGIWSTDILKDQKEPKNKTFLRCEAKNYSGRFTCWWLTTISTDLTFSVK
SSRGSSDPQGVTCGAATLSAERVRGDNKEYEYSVECQEDSACPAAEESLPIEVMVDAVHKLKYENYT
SSFFIRDIIKPDPPKNLQLKPLKNSRQVEVSWEYPDTWSTPHSYFSLTFCVQVQGKSKREKKDRVFTD
KTSATVICRKNASISVRAQDRYYSSSWSEWASVPCS (SEQ ID NO: 17)

p35
RNLPVATPDPGMFPCLHHSQNLLRAVSNMLQKARQTLEFYPCTSEEIDHEDITKDKTSTVEACLPLEL
TKNESCLNSRETSFITNGSCLASRKTSFMMALCLSSIYEDLKMYQVEFKTMNAKLLMDPKRQIFLDQN
MLAVIDELMQALNFNSETVPQKSSLEEPDFYKTKIKLCILLHAFRIRAVTIDRVMSYLNAS
(SEQ ID NO: 18)

Peptide linkers

GGGGSGGGGSGGGGS (SEQ ID NO: 19)
GSADGG (SEQ ID NO: 20)
GGSGG (SEQ ID NO: 21)
SSSSGSSSSGSSSSG (SEQ ID NO: 22)

Fig. 1b

IL-12 IMMUNOCONJUGATE

FIELD OF THE INVENTION

This invention relates to a conjugate for targeting an agent, such as a therapeutic or diagnostic agent, to tissues in vivo. In particular, it relates to conjugates for targeting the extra-cellular matrix (ECM) of tissues, particularly tumour neovasulature, and to therapeutic use of such conjugates in the treatment of a disease/disorder, such as cancer or pathological angiogenesis. In particular the invention relates to immunocytokines for targeting IL-12 to antigens selectively expressed in the ECM of the tumour neovasculature or sites of pathological angiogenesis.

BACKGROUND TO THE INVENTION

Cytokines are key mediators of innate and adaptive immunity. Many cytokines have been used for therapeutic purposes in patients with advanced cancer, but their administration is typically associated with severe toxicity, hampering dose escalation to therapeutically active regimens and their development as anticancer drugs. To overcome these problems, the use of 'immunocytokines' (i.e. cytokines fused to antibodies or antibody fragments) has been proposed, with the aim to concentrate the immune-system stimulating activity at the site of disease while sparing normal tissues[1-5].

The heterodimeric cytokine interleukin-12 (IL-12) is a key mediator of innate and cellular immunity with potent antitumour and antimetastatic activity[6-8]. It consists of a p35 and a p40 subunit covalently linked by a disulphide bridge.

Secretion of the isolated p35 subunit has never been detected; in contrast, the cells that produce the biologically active IL-12 heterodimer secrete p40 in free form in a 10-100-fold excess over the IL-12 heterodimer; depending on the stimulus[9]. A biological function of free p40 has never been observed and its physiological significance is still debated. Disulphide linked homodimers of p40 are produced in the mouse; murine p40 homodimers, in contrast to the free p40, have the ability to block IL-12 functions in vitro and in vivo[10]. The existence of human p40 homodimers has been demonstrated up to now only in p40 transfected cell lines and the physiological relevance of human p40 homodimers is still debated[11,12].

IL-12 acts primarily on T and NK cells. The most important functions of IL-12 are the priming of the T helper 1 (Th1) immune responses and IFN-γ secretion by NK cells[13].

IL-12 generates the Th1 response in three modalities: (i) it promotes the differentiation of naïve T cells, during initial encounter with an antigen, into a population of Th1-cells capable of producing large amounts of IFN-γ following activation[14], (ii) it serves as a costimulus required for maximum secretion of IFN-γ by differentiated Th1 cells responding to a specific antigen[15], and (iii) it stimulates the development of IFN-γ producing Th1 cells from populations of resting memory T cells interacting with an antigen to which they have been previously exposed[16].

IL-12 strongly inhibits neo-vascularisation and IFN-γ seems to play a critical role as a mediator of the anti-angiogenic effects of IL-12[17]. Interferon gamma-induced protein 10 (IP-10) is known to be a potent inhibitor of angiogenesis[18,19].

As with many other cytokines, however, the administration of recombinant human IL-12 is associated with severe toxicity, hampering its development as an anticancer drug. Clinical trials in patients with cancer have revealed promising therapeutic activities, but have also shown that recombinant human IL-12 is extremely toxic to humans, with a maximal tolerated dose of 0.5 μg/kg of body weight[20,21].

The toxic side effects of toxins, particularly cytokines such as such as IL-12 have made it difficult to administer an effective dose and to reach high concentrations at the site of a tumour.

Previously, researchers have attempted to overcome these drawbacks by targeting delivery of IL-12 to the tumour environment and in particular to tumour blood vessels (tumour vascular targeting). Tumour vascular targeting aims at disrupting the tumour vasculature, reducing blood flow to deprive the tumour of oxygen and nutrients, causing tumour cell death.

A targeted delivery of IL-12 to the tumour environment is expected to increase the therapeutic index of the cytokine. The concentration of cytokines, and in particular IL-12, at the level of tumour blood vessels is an attractive therapeutic strategy for a number of reasons.

First, the tumour neovasculature is more accessible to intravenously administered therapeutic agents than are tumour cells, which helps avoid problems associated with the interstitial hypertension of solid tumours[22].

Second, angiogenesis is characteristic of most aggressive solid tumours[23]. Angiogenesis describes the growth of new blood vessels from existing blood vessels. Tumours can induce angiogenesis through secretion of various growth factors (e.g. Vascular Endothelial Growth Factor). Tumour angiogenesis allows tumours to grow beyond a few millimeters in diameter and is also a prerequisite for tumour metastasis. New blood vessels formed as the result of angiogenesis form the neovasculature of the tumour or the tumour metastases. Targeting IL-12 to the neovasculature should allow the immunotherapy of a variety of different tumour types.

Third, IL-12 shows an anti-angiogenic activity conferred by its downstream mediator, IP-10[17,24].

The alternatively spliced extra domains A (ED-A) and B (ED-B) of fibronectin and the A1 domain of tenascin-C represent three of the best-characterised markers of angiogenesis and have been reported to be expressed around the neo-vasculature and in the stroma of virtually all types of aggressive solid tumours. Furthermore, even non-solid cancers, such as leukaemia, may be amenable to treatment by targeting antigens of the neovasculature. WO2011/015333 described treating leukaemia, including acute myeloid leukaemia, by targeting the bone marrow neovasculature.

Three human monoclonal antibodies specific to these targets have been developed and moved to clinical trials: L19 (specific to ED-B)[25], F8 (specific to ED-A)[26] and F16 (specific to the A1 domain of tenascin-C)[27].

In addition, several antibody derivatives, based on the modification of L19, F8 or F16 with cytokines or iodine radionuclides, are currently being investigated in Phase I and Phase II clinical trials in patients with cancer and with rheumatoid arthritis[28,29]. These biopharmaceuticals are called L19-[124]I, L19-$^{131}$I, L19-IL2, L19-TNF, F8-IL10, F16-[124]I, F16-$^{131}$I, F16-IL2, indicating the modular nature of these derivatives, in which the antibody moiety is used to deliver a payload at the site of disease.

In WO2008/120101 an I[125]-labelled F8 diabody was shown to selectively target I[125] to tumours in mice.

An F8-IL2 diabody conjugate has been shown to reduce tumour burden in mice (WO2008/120101, WO2010/078945).

Researchers have attempted to improve targeting of IL-12 to the vasculature using antibody-IL-12 conjugates. Halin et al. sequentially fused the p40 and p35 domains of the heterodimeric IL-12 using a (Ser$_4$Gly)$_3$ linker and appended at the N-terminal end of the antibody fragment scFv(L19). This immunocytokine showed an increased therapeutic activity of IL12; however, only a modest tumour targeting was observed[30].

Gafner et a(successfully cloned and tested a heterodimeric fusion protein in which the disulphide-linked p35 and p40 subunits were fused to scFv(L19)[31] to produce the fusion protein p40-scFv(L19)/scFv(L19)-p35 (see also WO2006/119897). This heterodimeric fusion protein showed an excellent tumour-targeting performance in biodistribution studies and enhanced therapeutic activity compared to the Halin format.

SUMMARY OF THE INVENTION

The present invention relates to a conjugate comprising a therapeutic or diagnostic agent portion, such as a cytokine, e.g. IL-12, and single chain targeting portion comprising two antigen binding sites, such as a single chain diabody.

More specifically, the present invention relates to a conjugate comprising linked interleukin 12 (IL-12) subunits p40 and p35 and a single chain targeting portion comprising two antigen binding sites.

One exemplary embodiment of the new format is a single chain protein comprising linked interleukin 12 (IL-12) subunits p40 and p35 and a single chain targeting portion comprising two antigen binding sites. The single chain protein may be a single chain fusion protein comprising linked IL-12 subunits p40 and p35 and a single chain targeting portion comprising two antigen binding sites.

The invention is derived from work which compared the tumour-targeting abilities of three antibody-IL-12 immunocytokine formats. Surprisingly, a new format was discovered, which improves tumour targeting ability compared with known formats. The new format also has the further advantages of easier production and purification.

As shown in the Examples, a single chain fusion protein comprising the p40 and p35 subunits of IL-12 linked to a single chain F8 diabody (p40p35F8F8), demonstrates improved tumour targeting in vivo compared with the scFv-IL-12-scFv immunocytokine format described by Gafner et al WO2006/119897. In contrast, an F8-IL-12 diabody (p40p35F8)×2, does not show any tumour uptake. These formats are illustrated in FIG. 2.

Thus, surprisingly, a single chain bivalent immunocytokine displays a better biodistribution profile compared with previously known formats. This is remarkable since the heterodimeric format described by Gafner et al. (WO2006/119897) already showed very good biodistribution, and it was unexpected that a new format could retain or even further improve this targeting profile.

A conjugate comprising the p40 and p35 subunits of IL-12 linked to a single chain targeting portion comprising two antigen binding sites displays excellent tumour targeting ability.

In addition, unlike the Gafner et al. heterodimeric format, the immunocytokine of the present invention can be expressed as a single chain polypeptide, for example as a single chain protein comprising linked IL-12 subunits p40 and p35 and a single chain targeting portion comprising two antigen binding sites. This format has the advantage of being easier to produce and purify since it consists of one single species. This facilitates production of clinical-grade material. Further, expression of a single chain immunocytokine avoids homodimerization of the p35 subunit, which can be associated with separate expression of the p35 and p40 subunits. Purification of a heterodimeric immunocytokine is facilitated by the use of peptidic tags, but these must be removed for clinical grade material. The immunocytokine of the present invention offers a simpler route to purification and production, while retaining and even improving on the biodistribution profile of previous products.

These results have significant therapeutic implications for improved targeting of IL-12 to tumours and to other sites of pathological angiogenesis. Conjugates of the invention may be used in the treatment of cancer or treatment of pathological angiogenesis. The wider implications also include a variety of other applications involving targeting of substances in vivo, including diagnostic methods as well as the prevention and treatment of diseases and other pathological conditions.

In a first aspect, the invention relates to a conjugate comprising linked interleukin 12 (IL-12) subunits p40 and p35 and a single chain targeting portion comprising two antigen binding sites.

The conjugate may be or may comprise a single chain protein. When the conjugate is a single chain protein, the entire protein can be expressed as a single polypeptide or fusion protein. For example, the conjugate may be a single chain protein comprising IL-12 subunits p40 and p35 and a single chain targeting portion comprising two antigen binding sites. Alternatively, the conjugate may comprise a heterodimeric agent (e.g. IL-12) linked to the single chain targeting portion. One subunit of the heterodimeric agent may be linked by a peptide bond or peptide linker to the single chain targeting portion, and thus expressed as a fusion protein, then assembled with the other subunit. For example, the conjugate may comprise heterodimeric IL-12 p40 and p35 subunits, and a single chain targeting portion linked to one of the subunits (e.g. p35), optionally by a peptide linker.

The linkage may be at the N or C end of the targeting portion. Suitable ways of linking are disclosed herein. Preferably the p35 subunit is linked to the single chain targeting portion.

Preferably the conjugate contains only one IL-12. Preferably the conjugate contains only one of each p35 and p40 subunit. Preferably the conjugate contains only one targeting portion. Preferably the targeting portion is bivalent, having only two antigen binding sites. The conjugate may be an immunocytokine, wherein one or preferably both of the antigen binding sites is provided by an antibody molecule. Preferably the targeting portion is a single chain diabody.

Preferably the targeting portion is linked to the C terminus of the p35 subunit. The conjugate may therefore have the format [p40]-[p35]-[targeting portion]. Preferably the p40 subunit has a free N terminus, as this arrangement has been shown to provide improved tumour targeting in vivo.

Preferably the targeting portion binds an extra-cellular matrix component associated with neoplastic growth and/or angiogenesis. For example, the targeting portion may bind fibronectin (e.g. domain ED-A or ED-B) or tenascin-C (e.g. domain A1).

The targeting portion may comprise an antigen binding site having the complementarity determining regions (CDRs) of antibody F8 set forth in SEQ ID NOs 9-14. The antigen binding site may comprise VH and/or VL domains of antibody F8 set forth in SEQ ID NOs 23 and 24, respectively. The targeting portion may comprise or consist of the F8 single chain diabody amino acid sequence set forth in SEQ ID NO: 31.

Other antibodies capable of binding to ECM proteins such as fibronectin, for example L19 (specific to ED-B), or F16

(specific to the A1 domain of tenascin-C) are known, and fragments of these antibodies, for example their CDRs, VH and/or VL domains, may be used in targeting portions in the present invention.

Preferably the conjugate has a molecular weight of less than 150 kDa, more preferably 140, 130, 120 kDa or less. Preferably the conjugate has a molecular weight of between 100 and 150 kDa, preferably between 100 and 120 kDa.

The conjugate may have least 70% sequence identity, more preferably one of at least 75%, 80%, 85%, 90%, 95%, 96%, 97%, 98%, 99% or 100%, sequence identity, to the amino acid sequence of p40p35F8F8 (SEQ ID NO: 8).

The conjugate may comprise or consist of the amino acid sequence set forth in SEQ ID NO: 8. The conjugate may be encoded by the nucleotide sequence consisting of or comprising SEQ ID NO: 1.

The invention also provides isolated nucleic acids encoding conjugates of the invention. Examples of encoding nucleic acid sequences are disclosed herein. An isolated nucleic acid and may be used to express the fusion protein of the invention, for example by expression in a bacterial, yeast, insect or mammalian host cell. A preferred host cell is *E. coli*. The encoded nucleic acid will generally be provided in the form of a recombinant vector for expression. Host cells in vitro comprising such vectors are part of the invention, as is their use for expressing the fusion proteins, which may subsequently be purified from cell culture and optionally formulated into a pharmaceutical composition.

A conjugate or immunocytokine of the invention may be provided for example in a pharmaceutical composition, and may be employed for medical use as described herein, either alone or in combination with one or more further therapeutic agents.

In another aspect the invention relates to a conjugate as herein described for use in a method of treating cancer or inhibiting angiogenesis by targeting IL-12 to the neovasculature in vivo.

In another aspect the invention relates to a method of treating cancer or inhibiting angiogenesis by targeting IL-12 to the neovasculature in a patient, the method comprising administering a therapeutically effective amount of a conjugate as herein described to the patient.

BRIEF DESCRIPTION OF THE FIGURES

FIG. 1b shows the amino acid sequence of the F8-IL12 fusion protein (p40p35F8F8). The sequence reads in the direction N-C of FIG. 1a. Each of the p40, p35, VH and VL subunits are joined by linker sequences, which are shown in grey. The two F8VH sequences are underlined. Each F8VH sequence is followed by a VL sequence. The VH and VL complementarity determining regions (CDR's), CDR1 VH, CDR2 VH, CDR3 VH and CDR1 VL, CDR2 VL and CDR3 VL are shown in boxes within the VH and VL sequences. The amino acid sequences of the CDR's are also indicated separately (SEQ ID NOs 9-14, respectively). The amino acid sequences of the F8-VH and F8-VL domains (SEQ ID NOs 15 and 16, respectively); the IL-12 p40 and p35 domains (SEQ ID NOs 17 and 18, respectively) and the peptide linkers(SEQ ID NOs 19-22) are also indicated separately below.

DETAILED DESCRIPTION

Figure 1A:
FIG. 1a shows a schematic representation of the F8-IL12 single chain diabody fusion protein (p40p35F8F8) (SEQ ID NO: 8), an exemplary embodiment of the present invention. In this embodiment, the IL-12 p40 and p35 subunits were fused using a linker sequence (peptide/amino acid linker) and connected via a linker to two sets of F8 antibody fragments (two VH-VL sets). Each VH and VL within the set is connected by a linker between the variable heavy (F8 VH) and variable light (F8-VL) chains. The linkers within each set are not long enough to allow pairing between the VH and VL domains. Each VL-VL set is connected by a linker which is long enough to allow pairing between the VH and VL domains of the first set with the complementary VH and VL domains of the second set. The amino acid linkers are shown as black rectangles.

The invention includes the combination of the aspects and preferred features described except where such a combination is clearly impermissible or expressly avoided.

In one aspect the invention relates to a conjugate comprising a therapeutic or diagnostic agent portion, such as IL-12, and single chain targeting portion comprising two antigen binding sites, such as a single chain diabody.

Conjugate

Conjugates of the invention comprise a therapeutic or diagnostic agent portion, such as IL-12, and single chain targeting portion comprising two antigen binding sites.

The conjugate may be or may comprise a single chain protein. When the conjugate is a single chain protein, the entire protein can be expressed as a single polypeptide. For example, the conjugate may be a single chain protein comprising IL-12 subunits p40 and p35 and a single chain targeting portion comprising two antigen binding sites. The single chain protein may be a fusion protein, for example a single chain fusion protein comprising linked IL-12 p35 and p40 subunits, and single chain targeting portion comprising two antigen binding sites. By "single chain fusion protein"

is meant a polypeptide that is a translation product resulting from the fusion of two or more genes or nucleic acid coding sequences into one open reading frame (ORF). The fused expression products of the two genes in the ORF may be conjugated by a peptide linker encoded in-frame. Suitable peptide linkers are described herein.

However, it is also envisaged that the therapeutic or diagnostic agent need not be a single chain. For example, the IL-12 p40 and p35 subunits may be a heterodimer. The heterodimer may be linked to the N or the C end of the single chain targeting portion. The heterodimer may be linked to the single chain targeting portion via the p40 or p35 subunit. The linkage may be direct or may be indirect, for example via a peptide linker. Optionally, one of the p35 or p40 subunits may be linked to the single chain targeting agent so that one subunit is expressed with the single chain targeting agent, and the second subunit is a second polypeptide chain. Thus, the first and second subunits may form a heterodimer, e.g. linked by one or more disulphide bonds. One subunit may be linked to the N or C end of the targeting portion either directly or indirectly, for example via a peptide linker. Suitable linkers and ways of linking are disclosed herein. Preferably the p35 subunit is linked to the single chain targeting portion.

Targeting Portion

The targeting portion is a single chain targeting portion. The targeting portion may comprise an antibody molecule or a fragment thereof, for example a single chain diabody.

The term "antibody molecule" describes an immunoglobulin whether natural or partly or wholly synthetically produced. The term also covers any polypeptide or protein having a binding domain which is, or is substantially homologous to, an antibody binding domain. Examples of antibodies are the immunoglobulin isotypes and their isotypic subclasses; fragments which comprise an antigen binding domain such single chain diabodies. The antibody molecule or fragment thereof may be human or humanised. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which mayor may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

The term "specific" may be used to refer to the situation in which one member of a specific binding pair will not show any significant binding to molecules other than its specific binding partner(s). The term is also applicable where e.g. an antigen-binding site is specific for a particular epitope that is carried by a number of antigens, in which case the targeting portion carrying the antigen-binding site will be able to bind to the various antigens carrying the epitope.

The targeting portion may be bivalent i.e. has two antigen binding sites. An "antigen binding site" describes the part of an antibody which comprises the area which specifically binds to and is complementary to part or all of an antigen. Where an antigen is large, an antibody may only bind to a particular part of the antigen, which part is termed an epitope. An antigen binding site may be provided by one or more antibody variable domains (e.g. a so-called Fd antibody fragment consisting of a VH domain). Preferably, an antigen binding site comprises an antibody light chain variable region (VL) and an antibody heavy chain variable region (VH).

The targeting portion may comprise two antigen binding sites, which may be identical or different. Preferably, the targeting portion comprises two antigen binding sites, wherein each binding site is provided by a VH-VL domain pair. For example, a targeting portion may comprise two identical VH-VL domain pairs.

Each of the antigen binding sites in the targeting portion may bind the same antigen or epitope. This can be achieved by providing two identical antigen binding sites, or by providing two different antigen binding sites, for example comprising different VH and VL domains, which nevertheless both bind the same antigen or epitope. Alternatively the targeting portion may be bispecific, for example it may be a bispecific single chain diabody. By 'bispecific" we mean that each of the antigen binding sites binds a different antigen. Optionally, two antigen binding sites may bind two different antigens mentioned herein, e.g. two different antigens of the extracellular matrix, or two different domains of a particular antigen (e.g. fibronectin or tenascin-C).

Preferably the targeting portion comprises or consists of a single chain diabody.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804, also reference numbers 35 and 36).

Figure 2:
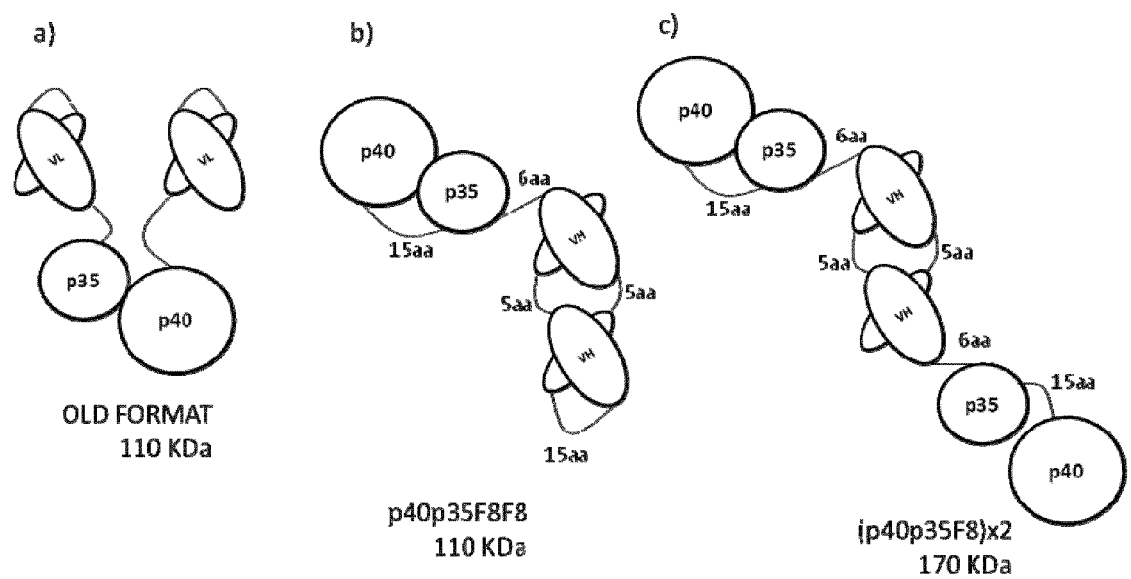
FIG. 2 shows (A) the structure of the scFv-p30:p40-scFv heterodimeric immunocytokine format described by Gafner et al. ('old format'); (B) a single chain p40p35F8F8 fusion protein according to the invention; and (C) F8 diabody (p40p35F8F8)×2.
Figure 7:
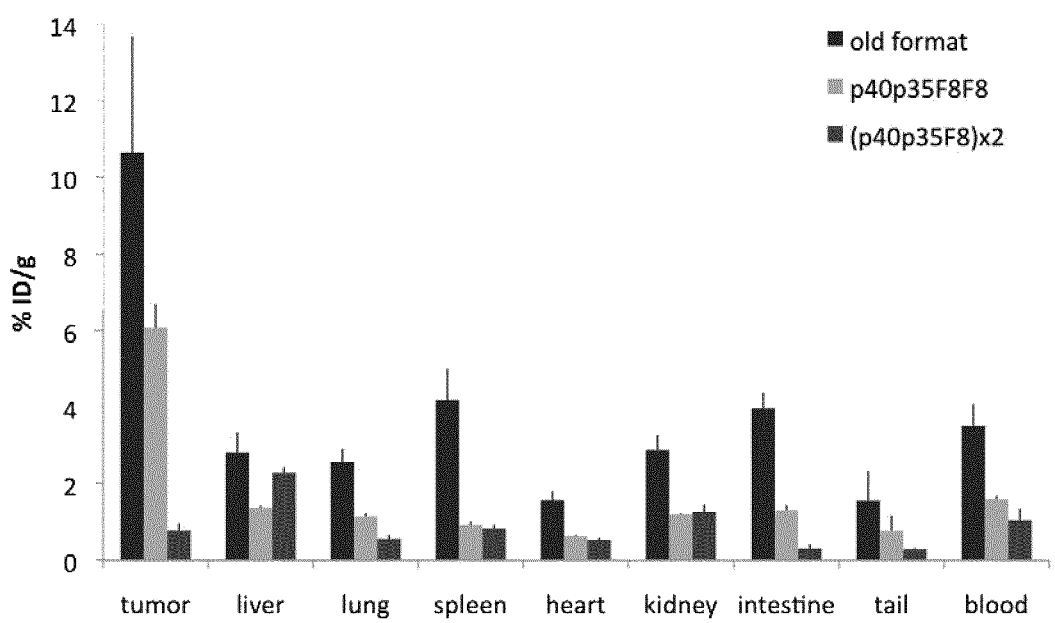
FIG. 7 shows a comparison of the in vivo targeting performance of the old heterodimeric format (scFv-IL-12-scFv), the new p40p35F8F8 format and the new (p40p35F8F8)×2 format in a mouse tumour model. The results are presented in the order: old format (black bar), p40p35F8F8 (light grey), (p40p35F8F8)×2 (dark grey).

In a diabody a heavy chain variable domain (VH) is connected to a light chain variable domain (VL) on the same polypeptide chain. The VH and VL domains are connected by a peptide linker that is too short to allow pairing between the two domains (generally around 5 amino acids). This forces paring with the complementary VH and VL domains of another chain. An example of this format is found in the (p40p35F8)×2 protein shown in FIG. 2 (C). As shown in FIG. 7, this protein did not show tumour targeting in vivo.

Whereas normal diabodies are unsuitable for use in the present invention, a single chain diabody is suitable and represents a preferred embodiment of the invention. In a single chain diabody two sets of VH and VL domains are connected together in sequence on the same polypeptide chain. For example, the two sets of VH and VL domains may be assembled in a single chain sequence as follows:

(VH-VL)-(VH-VL), where the brackets indicate a set.

In the single chain diabody format each of the VH and VL domains within a set is connected by a short or 'non-flexible' peptide linker. This type of peptide linker sequence is not long enough to allow pairing of the VH and VL domains within the set. Generally a short or 'non flexible' peptide linker is around 5 amino acids.

The two sets of VH and VL domains are connected as a single chain by a long or 'flexible' peptide linker. This type of peptide linker sequence is long enough to allow pairing of the VH and VL domains of the first set with the complementary VH and VL domains of the second set. Generally a long or 'flexible' linker is around 15 amino acids.

Single chain diabodies have been previously generated[38]. A bispecific single chain diabody has been used to target adenovirus to endothelial cells[37].

Diabodies and single chain diabodies can be expressed in and secreted from E. coli, thus allowing the easy production of large amounts of the said fragments.

The targeting portion may bind an extra-cellular matrix (ECM) component associated with neoplastic growth and/or angiogenesis.

Preferably the targeting portion binds fibronectin. Fibronectin is an antigen subject to alternative splicing, and a number of alternative isoforms of fibronectin are known, including alternatively spliced isoforms A-FN and B-FN, comprising domains ED-A or ED-B respectively, which are known markers of angiogenesis. The targeting portion may selectively bind to isoforms of fibronectin selectively expressed in the neovasculature. An antigen binding site in the targeting portion of the invention may bind fibronectin isoform A-FN, e.g. it may bind domain ED-A (extra domain A). An antigen binding site in the targeting portion of the invention may bind fibronectin isoform B-FN, e.g. it may bind ED-B (extra domain B).

Fibronectin Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN[34]. ED-A is mainly absent in the plasma form of FN but is abundant during embryogenesis, tissue remodelling, fibrosis, cardiac transplantation and solid tumour growth.

Fibronectin isoform B-FN is one of the best known markers angiogenesis (U.S. Ser. No. 10/382,107, WO01/62298). An extra domain "ED-B" of 91 amino acids is found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues.

The targeting portion may bind tenascin-C. Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis. Several isoforms of tenascin-C can be generated as a result of alternative splicing which may lead to the inclusion of (multiple) domains in the central part of this protein, ranging from domain A1 to domain D (Borsi L et al Int J Cancer 1992; 52:688-692, Carnemolla B et al. Eur J Biochem 1992; 205:561-567, WO2006/050834). An antigen binding site in the targeting portion of the present invention may bind tenascin-C domain A1.

The targeting portion may comprise an antigen binding site having the complementarity determining regions (CDRs), or the VH and/or VL domains of an antibody capable of specifically binding to an antigen of interest, for example, one or more CDRs or VH and/or VL domains of an antibody capable of specifically binding to an antigen of the ECM. The antigen may be an antigen preferentially expressed by cells of a tumour or tumour neovasculature or associated with the ECM. Such antigens include fibronectin and tenascin C, as described above.

Thus, the targeting portion may comprise an antigen binding site of the antibody F8, the antibody L19 or the antibody F16, which have all been shown to bind specifically to ECM antigens. The targeting portion may comprise an antigen binding site having one, two, three, four, five or six CDR's, or the VH and/or VL domains of antibody F8, L19 or F16.

F8 is a human monoclonal scFv antibody fragment specific to the alternatively spliced ED-A domain of fibronectin and has been previously described[33]. L19 is a human monoclonal scFv specific to the A1 domain of Tenascin C and has been previously described (WO2006/050834). F16 is a human monoclonal scFv specific to the alternatively spliced ED-A domain of fibronectin and has been previously described (WO2006/119897).

An antigen binding site may comprise one, two, three, four, five or six CDRs of antibody F8. Amino acid sequences of the CDRs of F8 are:
SEQ ID NO:9 (CDR1 VH);
SEQ ID NO:10 (CDR2 VH);
SEQ ID NO:11 (CDR3 VH);
SEQ ID NO:12 (CDR1 VL);
SEQ ID NO:13 (CDR2 VL), and/or
SEQ ID NO:14 (CDR3 VL).

SEQ ID NOs 9-11 are the amino acid sequences of the VH CDR regions (1-3, respectively) of the human monoclonal antibody F8. SEQ ID NOs 12-14 are the amino acid of the VL CDR regions (1-3, respectively) of the human monoclonal antibody F8. The CDRs of F8 shown in SEQ ID NOs 9-14 are encoded by the nucleotide sequences shown in SEQ ID NOs 2-7, respectively.

The amino acid sequence of the VH and VL domains of antibody F8 are shown in FIG. 1b. The amino acid sequence of the VH and VL domains of F8 correspond to SEQ ID NO: 15 and SEQ ID NO:16, respectively. The nucleotide sequences of the VH and VL domains of F8 correspond to SEQ ID NO: 23 and SEQ ID NO: 24, respectively.

An antigen binding site may comprise one, two, three, four, five or six CDRs of antibody L19. Amino acid sequences of the CDRs of L19 are:
SEQ ID NO:35 (CDR1 VH);
SEQ ID NO:36 (CDR2 VH);

SEQ ID NO:37 (CDR3 VH);
SEQ ID NO:38 (CDR1 VL);
SEQ ID NO:39 (CDR2 VL), and/or
SEQ ID NO:40 (CDR3 VL).

SEQ ID NOs 35-37 are the amino acid sequences of the VH CDR regions (1-3, respectively) of the human monoclonal antibody L19. SEQ ID NOs 38-40 are the amino acid of the VL CDR regions (1-3, respectively) of the human monoclonal antibody L19.

The amino acid sequence of the VH and VL domains of antibody L19 correspond to SEQ ID NO: 33 and SEQ ID NO:34, respectively. The amino acid sequence of the scFv (L19) is given in SEQ ID NO: 41).

An antigen binding site may comprise one, two, three, four, five or six CDRs of antibody F16. Amino acid sequences of the CDRs of F16 are:
SEQ ID NO:44 (CDR1 VH);
SEQ ID NO:45 (CDR2 VH);
SEQ ID NO:46 (CDR3 VH);
SEQ ID NO:47 (CDR1 VL);
SEQ ID NO:48 (CDR2 VL), and/or
SEQ ID NO:49 (CDR3 VL).

SEQ ID NOs 44-46 are the amino acid sequences of the VH CDR regions (1-3, respectively) of the human monoclonal antibody F16. SEQ ID NOs 47-49 are to the amino acid of the VL CDR regions (1-3, respectively) of the human monoclonal antibody F16.

The amino acid sequence of the VH and VL domains of antibody F16 correspond to SEQ ID NO: 42 and SEQ ID NO:43, respectively.

The conjugate may comprise linked p35 and p40 subunits of IL-12 joined to a single chain diabody, for example a single chain diabody comprising the VH and VL domains of antibody F8, L19 or, F16.

A single chain diabody according to the invention may have a VH domain having at least 70%, more preferably one of at least 75%, 80%, 85%, 90%, 95%, 96%, 97%, 98%, 99% or 100%, sequence identity to the F8 VH domain amino acid sequence SEQ ID NO:15, the L19 VH domain amino acid sequence SEQ ID NO: 33, or the F16 VH domain amino acid sequence SEQ ID NO: 42. The VH domain may be encoded by a nucleotide sequence having at least 70%, more preferably one of at least 75%, 80%, 85%, 90%, 95%, 96%, 97%, 98%, 99% or 100%, sequence identity to the F8 VH domain nucleotide sequence set forth in SEQ ID NO: 23.

A single chain diabody according to the invention may have a VL domain having at least 70%, more preferably one of at least 75%, 80%, 85%, 90%, 95%, 96%, 97%, 98%, 99% or 100%, sequence identity to the F8 VL domain amino acid sequence SEQ ID NO:16, the L19 amino acid sequence SEQ ID NO: 34 or the F16 amino acid sequence SEQ ID NO: 43. The VL domain may be encoded by a nucleotide sequence having at least 70%, more preferably one of at least 75%, 80%, 85%, 90%, 95%, 96%, 97%, 98%, 99% or 100%, sequence identity to the F8 VL domain nucleotide sequence set forth in SEQ ID NO: 24.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Variants of these VH and VL domains and CDRs may also be employed in antibody molecules for use in conjugates as described herein. Suitable variants can be obtained by means of methods of sequence alteration, or mutation, and screening.

Particular variants for use as described herein may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1.

Alterations may be made in one or more framework regions and/or one or more CDRs. In particular, alterations may be made in VH CDR1, VH, CDR2 and/or VH CDR3.

The amino acid sequence of the F8 single chain diabody is found in SEQ ID NO: 32. The F8 single chain diabody may comprise or consist the amino acid sequence of SEQ ID NO: 32. The nucleotide sequence encoding the F8 single chain diabody is found in SEQ ID NO: 31.

A single chain diabody according to the invention may have at least 70%, more preferably one of at least 75%, 80%, 85%, 90%, 95%, 96%, 97%, 98%, 99% or 100%, sequence identity to the amino acid sequence of the F8 single chain diabody set forth in SEQ ID NO:32. It may be encoded by a nucleotide sequence having at least 70%, more preferably one of at least 75%, 80%, 85%, 90%, 95%, 96%, 97%, 98%, 99% or 100%, sequence identity to the nucleotide sequence set forth in SEQ ID NO:31.

Linkers

The targeting portion and therapeutic or diagnostic agent portion may be connected to each other directly, for example through any suitable chemical bond or through a linker, for example a peptide linker.

The peptide linker may be a short (2-20, preferably 2-15) residue stretch of amino acids). Suitable examples of peptide linker sequences are known in the art. One or more different linkers may be used. The linker may be about 5 amino acids in length. An example of a suitable linker is GSADGG (SEQ ID NO: 20) which is encoded by the nucleotide sequence SEQ ID NO:28.

The chemical bond may be, for example, a covalent or ionic bond. Examples of covalent bonds include peptide bonds (amide bonds) and disulphide bonds. For example the targeting portion and therapeutic or diagnostic agent portion may be covalently linked. For example by peptide bonds (amide bonds). Thus, the targeting portion and therapeutic or diagnostic agent portion may be produced (secreted) as a single chain polypeptide. The individual components that form the targeting portion or the therapeutic or diagnostic agent portion may also be connected directly, for example through any suitable chemical bond, or through a linker, for example a peptide linker. Examples of individual components which may be linked within the targeting portion are CDRs or VH or VL sequences. Examples of individual components within the therapeutic or diagnostic agent portion are cytokine subunits, such as the IL-12 p35 and p40 subunits.

For example, when the targeting portion comprises two sets of VH and VL sequences, for example where it is a single chain diabody, preferably the first and second set of VH and VL sequences are connected by a flexible peptide linker. By "flexible" is meant a linker sequence that is long enough to allow pairing of the VH and VL domains of the first set with the complementary VH and VL domains of the second set. An example of such a linker is SSSSGSSSSGSSSSG (SEQ ID NO: 22), which is encoded by the nucleotide sequence SEQ ID NO: 30. Preferably the VH-VL sequences within each set are connected by a 'non-flexible' linker. By a 'non-flexible' linker is meant a peptide linker sequence that is not long enough to allow pairing of the VH and VL domains. An example of a short linker sequence is GGSGG (SEQ ID NO: 21) which is encoded by the nucleotide sequence SEQ ID NO: 29. Individual cytokine subunits, such as the p40 and p35 domains of IL-12, may also be connected by a linker sequence. An example of a suitable linker sequence is GGGGSGGGGSGGGGS (SEQ ID NO: 19), which is encoded by the nucleotide sequence SEQ ID NO: 27.

Molecular Weight

Methods of determining the molecular weight of a protein are known in the art, for example SDS-PAGE. This may be the actual measured molecular weight with or without glycosylation. An example of a method for determining molecular weight is SDS-PAGE as described in Example 1 and shown in FIG. 6. Alternatively, molecular weight may be an estimated value based on e.g. the expected molecular weight of the conjugate with or, normally, without glycosylation. Methods for determining molecular weight can be found in standard textbooks for example Molecular biomethods handbook, second edition (2008) Humana Press, edited by John M. Walker and Ralph Rapley.

Therapeutic or Diagnostic Agent

The therapeutic or diagnostic agent may comprise a cytokine. Preferably the therapeutic or diagnostic agent comprises two subunits (i.e. a pair or subunits), for example the p40 and p35 subunits of IL-12.

The therapeutic or diagnostic agent may be a single chain protein, for example a single chain fusion protein. For example, p35 and p40 subunits of IL-12 may be linked (e.g. directly or by a peptide linker sequence) as a single polypeptide chain. Alternatively only one of the p35 or p40 subunits may be produced (expressed) as a single chain protein together with the single chain targeting portion. The second subunit is a second polypeptide chain, which is then linked to the first subunit as a heterodimer. The subunits of the heterodimer, e.g. IL-12 p35 and p40 subunits may be covalently linked. Forms of covalent linkage are described elsewhere herein. Preferably, when heterodimeric IL-12 is used in a conjugate of the invention, the subunits are linked by one or more disulphide bonds. Disulphide bonds link the subunits of natural IL-12, and thus this native form may be advantageous for functional activity.

IL-12 p35 and p40 Subunits.

Preferably the therapeutic agent is IL-12, or a subunit or subunits thereof. IL-12 or subunits thereof useful in the invention may be derived from any animal, e.g. human, rodent (e.g. rat, mouse), horse, cow, pig, sheep, dog, etc. Human IL-12 is preferred in conjugates for administration to humans. IL-12 occurs naturally as a heterodimeric protein composed of a 40 kDa (p40) subunit and a 35 kDa (p35) subunit. The actual molecular weights of the subunits may vary, e.g. when expressed in different species and depending on whether the protein is glycosylated and on the glycosylation pattern. The terms "p40" and "p35" therefore do not imply that the subunits have molecular weights of exactly 40 and 35 kDa respectively. Instead, these terms are used to identify and distinguish the two subunits of IL-12, which may more accurately be defined in terms of their amino acid sequences.

The amino acid sequence of the IL-12 p40 subunit is set out in SEQ ID NO: 17; the amino acid sequence of the IL-12 p35 subunit is set out in SEQ ID NO: 18. The nucleotide sequence encoding the IL-12 p40 subunit is set out in SEQ ID NO: 25; the nucleotide sequence encoding the IL-12 p35 subunit is set out in SEQ ID NO: 26.

Typically, the p35 subunit has at least 70%, more preferably one of at least 75%, 80%, 85%, 90%, 95%, 96%, 97%, 98%, 99% or 100%, sequence identity to the amino acid sequence shown in SEQ ID NO:18. The p35 subunit may be encoded by a nucleotide sequence having least 70%, more preferably one of at least 75%, 80%, 85%, 90%, 95%, 96%, 97%, 98%, 99% or 100%, sequence identity to SEQ ID NO:26.

The p40 subunit may have at least 70%, more preferably one of at least 75%, 80%, 85%, 90%, 95%, 96%, 97%, 98%, 99% or 100%, sequence identity to the amino acid sequence shown in SEQ ID NO:17. The p40 subunit may be encoded by a nucleotide sequence having least 70%, more preferably one of at least 75%, 80%, 85%, 90%, 95%, 96%, 97%, 98%, 99% or 100%, sequence identity to the nucleotide sequence shown in SEQ ID NO:25.

IL12 in conjugates of the invention retains a biological activity of IL12, e.g. an ability to act as a growth factor for activated T and NK cells, to enhance the lytic activity of NK/lymphokine-activated killer cells, to stimulate production of IFN-y by resting PMBC, to inhibit angiogenesis (e.g. through the downstream mediator IP-1 0), and/or to inhibit tumour growth and/or metastasis.

The therapeutic agent may comprise a single IL-12 fusion protein comprising linked IL-12 p35 and p40 subunits.

The subunits may be linked together by any suitable chemical bond. For example a covalent or ionic bond. Example of covalent bonds include peptide bonds (amide bonds) and disulphide bonds.

The p35 and p40 subunits of IL-12 may be covalently linked. The covalent linkage may be one or more disulphide bonds. The invention therefore allows the use and maintenance of a natural format of the IL-12 subunits in the conjugate.

Alternatively, the p35 and p40 subunits of IL-12 may be linked by peptide bonds (amide bonds), optionally through a peptide linker, as described above. Thus, the p35 and p40 subunits may be produced (secreted) as a single chain polypeptide.

The therapeutic or diagnostic agent may comprise or consist of IL-12 p35 and p40 subunits. The subunits may be a single chain, for example a p35 and p40 single chain fusion protein. The therapeutic or diagnostic agent may comprise or consist of p35 and p40 subunits as a heterodimer (heterodimeric protein).

The p35 and p40 subunits of IL-12 may be linked together in either order. For example, the N terminus of the p35 subunit may be conjugated to the C terminus of the p40 subunit or the N terminus of the p40 subunit may be conjugated to the C terminus of the p35 subunit. Preferably, the N terminus of the p35 subunit is conjugated to the C terminus of the p40 subunit.

The targeting portion may be conjugated to only one of the p40 or p35 subunits.

The targeting portion may be conjugated to either the C or the N terminus of p40 subunit or p35 subunit, depending on the relative orientation of the linked IL-12 subunits in the conjugate. For example, the targeting portion may be conjugated to the C terminus of the p35 subunit, the C terminus of the p40 subunit, the N terminus of the p40 subunit, or the N terminus of the p35 subunit. Preferably the targeting portion is conjugated to the C terminus of the p35 subunit.

The subunit which is not conjugated to the targeting portion may have a free amino or carboxyl terminus. Again this depends on the order that the subunits are linked together. For example, when the targeting portion is conjugated to the C terminus of the p35 subunit, the p40 subunit may have a free N terminus. When the targeting portion is conjugated to the C terminus of the p40 subunit, the p35 subunit may have a free N terminus. When the targeting portion is conjugated to the N terminus of the p40 subunit, the p35 subunit may have a free N terminus. When the targeting portion is conjugated to the N terminus of the p35 subunit, the p40 subunit may have a free N terminus.

Preferably the targeting portion is linked to the p35 subunit. Preferably the p40 subunit has a free (unfused) N terminus. When the p40 subunit has a free N terminus this is believed to maximise its activity.

Methods of Treatment

In a second aspect, a conjugate according to the invention may be used in a method of treatment of the human or animal body, such as a method of treatment (which may include prophylactic treatment) of a disease or disorder in a patient (typically a human patient) comprising administering the conjugate to the patient.

Accordingly, such aspects of the invention provide methods of treatment comprising administering a conjugate of the invention, pharmaceutical compositions comprising such a conjugate for the treatment of a condition or disease, and a method of making a medicament or pharmaceutical composition comprising formulating the conjugate of the present invention with a physiologically acceptable carrier or excipient.

Thus, a conjugate as herein described may be used in a method of treating cancer or inhibiting angiogenesis by targeting an agent to the neovasculature in vivo. The agent may be any therapeutic or diagnostic agent discussed herein. In particular a cytokine, such as IL-12.

Thus, a conjugate as herein described may be used in a method of treating cancer or inhibiting angiogenesis by targeting IL-12 to the neovasculature in vivo. Also contemplated is a method of treating cancer or inhibiting angiogenesis by targeting an agent, in particular a therapeutic agent e.g. IL-12, to the neovasculature in a patient, the method comprising administering a therapeutically effective amount of a conjugate as herein described to the patient.

Conditions treatable using the conjugate as described herein include cancer, other tumours and neoplastic conditions. The conjugate may be used to inhibit angiogenesis and thereby treat rheumatoid arthritis, diabetic retinopathy, age-related muscular degeneration, angiomas, tumours and cancer. Treatment may include prophylactic treatment. The conjugate may also be administered in diagnostic methods, e.g. targeting and diagnosis of angiogenesis, which may be associated with any of the above conditions. Other diseases and conditions may also be diagnosed and treated, according to the nature of the protein therapeutic or diagnostic agent contained in the conjugate, and the specificity of the targeting portion.

Cancers suitable for treatment as described herein include any type of solid or non-solid cancer or malignant lymphoma and especially liver cancer, lymphoma, leukaemia (e.g. acute myeloid leukaemia), sarcomas, skin cancer, bladder cancer, breast cancer, uterine cancer, ovarian cancer, prostate cancer, lung cancer, colorectal cancer, cervical cancer, head and neck cancer, oesophageal cancer, pancreatic cancer, renal cancer, stomach cancer and cerebral cancer. Cancers may be familial or sporadic. Cancers may be metastatic or non-metastatic.

Preferably, the cancer is a cancer selected from the group of kidney cancer, breast cancer, liver cancer, lung cancer, lymphoma, sarcoma (e.g. gastrointestinal stromal tumour), skin cancer (e.g. melanoma), colorectal cancer, and neuroendocrine tumours.

The cancer may express an isoform of fibronectin comprising domain ED-A or ED-B, or alternatively spliced tenascin-C comprising for example domain A1. Preferably the cancer expresses the ED-A isoform of fibronectin.

Expression of the ED-A isoform of fibronectin has been reported in a number of different cancers including kidney cancer, breast cancer, liver cancer, fibrosarcoma, rhabdomyosarcoma and melanoma (Lohi et al. 1995, Jacobs et al. 2002, Matsumoto et al. 1999, Oyama et al. 1989, Tavian et al. 1994, Borsi et al. 1987).

Pharmaceutical Compositions

A further aspect of the present invention relates to a pharmaceutical composition comprising at least one conjugate of the invention and optionally a pharmaceutically acceptable excipient.

Pharmaceutical compositions of the present invention typically comprise a therapeutically effective amount of a conjugate according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients. The pharmaceutical preparation of the invention may be adapted, for example, for parenteral use and may be administered to the patient in the form of solutions or the like.

Compositions comprising the conjugate of the present invention may be administered to a patient. Administration is preferably in a "therapeutically effective amount", this being sufficient to show benefit to the patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Treatments may be repeated at daily, twice-weekly, weekly, or monthly intervals at the discretion of the physician Conjugates of the invention may be administered to a patient in need of treatment via any suitable route, usually by injection into the bloodstream and/or directly into the site to be treated, e.g. tumour or tumour vasculature. The precise dose and its frequency of administration will depend upon a number of factors, the route of treatment, the size and location of the area to be treated (e.g. tumour).

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine, or anti-emetics.

Kits

Another aspect of the invention provides a therapeutic kit for use in the treatment of cancer or angiogenesis comprising a conjugate as described herein. The components of a kit are preferably sterile and in sealed vials or other containers.

A kit may further comprise instructions for use of the components in a method described herein. The components of the kit may be comprised or packaged in a container, for example a bag, box, jar, tin or blister pack.

Terminology

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Various further aspects of the present invention will be apparent to those skilled in the art in view of the present disclosure.

The present invention will now be illustrated by way of the following non-limiting examples.

EXAMPLES

Here we describe the production and characterisation of F8-IL-12 conjugates in two different formats and a comparison of these two formats with an old format F8-IL-12, thereby demonstrating the superiority of the single chain diabody format as claimed herein for in vivo targeting.

Example 1

Cloning of Two New IL-12 Based Immunocytokines

Figure 3A:
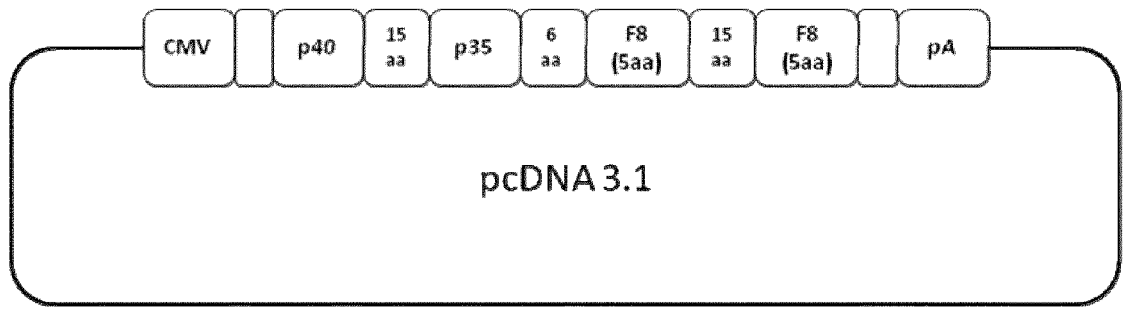
FIG. 3a shows the cloning strategy of p40p35F8F8

Cloning of p40p35F8F8:

The p40 and the p35 subunit of IL-12 were fused using 15 amino acid linker. Two scFv(F8) antibody fragments containing a short 5 amino acid linker between heavy and light chain were connected using a 15 amino acid linker. This single chain diabody fragment was then linked to the p35p40 fusion protein via a 6 amino acid linker. The cloning strategy is shown in FIG. 3a. The construct was cloned into vector pcDNA 3.1 for mammalian cell expression.

Figure 3B:
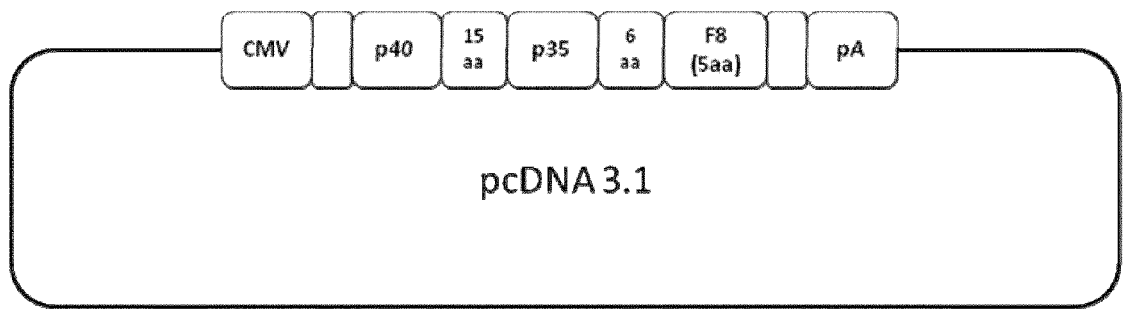
FIG. 3b shows the cloning strategy of (p40p35F8F8)×2

Cloning of (p40p35F8)×2:

The p40 and the p35 subunit of IL-12 were connected using 15 amino acid linker and fused to the N terminus scFv(F8) diabody using a 6 amino acid linker. The cloning strategy is shown in FIG. 3b. The construct was cloned into vector pcDNA 3.1.

Both the p40p35F8F8 and (p40p35F8)×2 proteins were successfully purified from medium by protein A affinity chromatography and analysed by SDS-PAGE and fast protein liquid chromatography gel filtration using a Superdex™ 200 10/300 GL size exclusion column.

Figure 5:
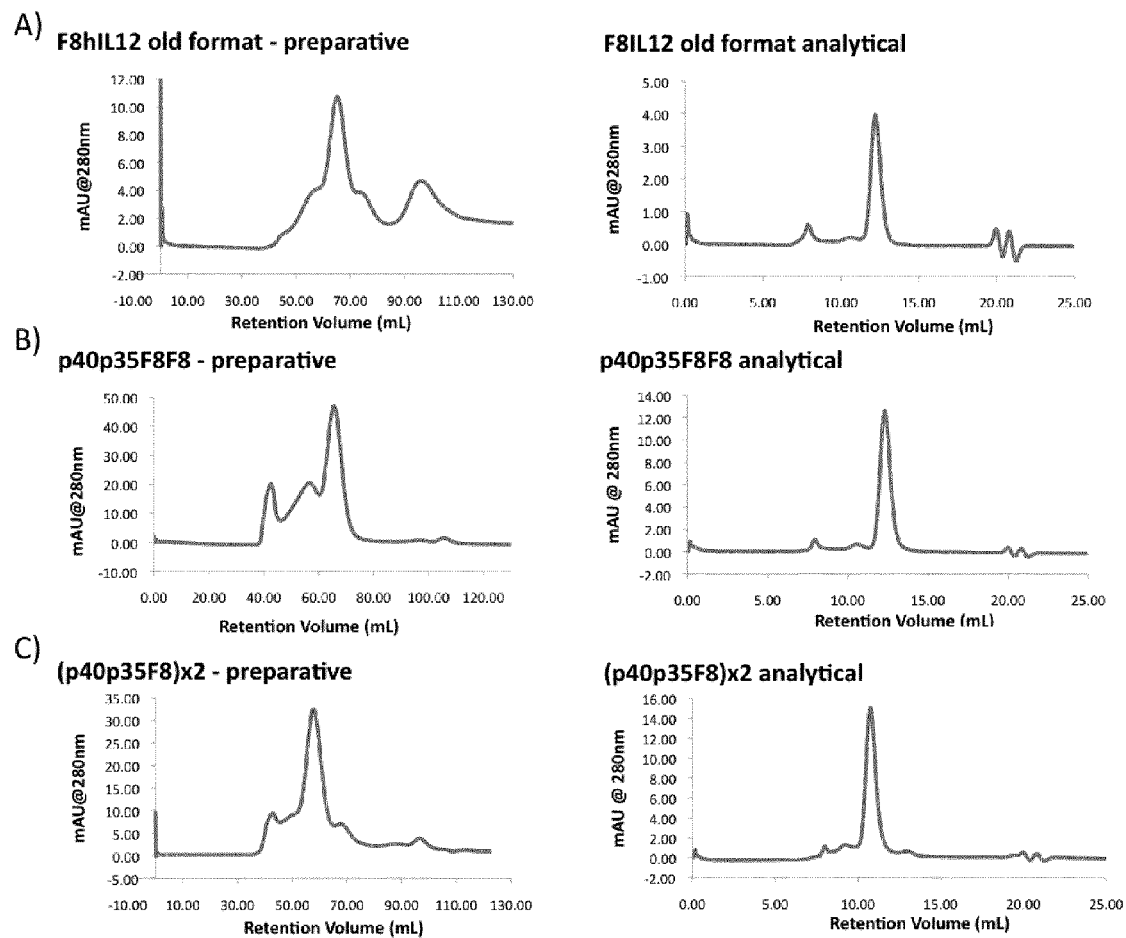
FIG. 5 shows gel filtration profiles of the IL-12 single chain diabody format and the IL-12 diabody format compared with the old format. A) shows a preparative and analytical profile of the F8hIL12 format (old format). B) and C) show preparative and analytical profiles of the two new formats. B) shows the p40p35F8F8 single chain diabody format, C) shows the (p40p35F8F8)×2 diabody format.

The gel filtration profiles of the p40p35F8F8 and (p40p35F8)×2 proteins are shown in FIG. 5 together with the gel filtration profile of the 'old format' F8 IL-12 protein. The results shown in FIG. 5 demonstrate that it is easier to purify the p40p35F8F8 protein compared to the F8 IL-12 protein in the old format.

Figure 6:
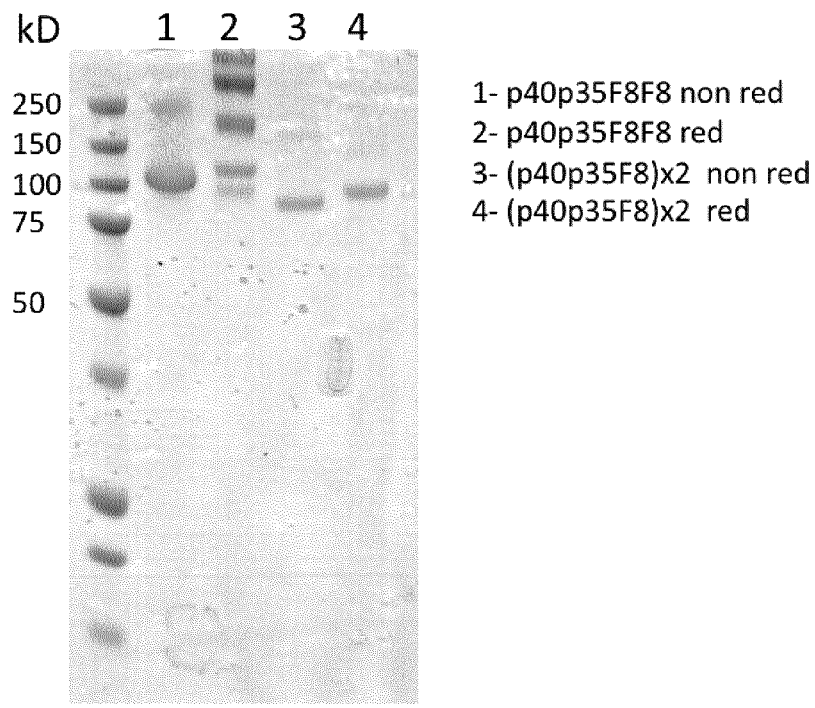
FIG. 6 shows SDS page in reducing and non-reducing conditions for the p40p35F8F8 protein (lanes 1 and 2) (p40p35F8F8)×2 protein (lanes 3 and 4). Lanes 1 and 3 show the protein under non reducing conditions, lanes 2 and 4 shows the protein under reducing conditions. The calculated molecular mass of p40p35F8F8 is 110 kDa, the calculated molecular mass of the dimeric (p40p35F8F8)×2 is 170 kD.

Using SDS page in reducing and non-reducing conditions the calculated molecular mass of p40p35F8F8 was found to be 110 kDa and the calculated molecular mass of the dimeric (p40p35F8)×2 was found to be 170 kD (FIG. 6).

Example 2

Calculating the KD Value of p40p35F8F8

The apparent KD value of the single chain fusion protein p40p35F8F8 was determined by Biacore on an antigen-coated chip.

Figure 4:
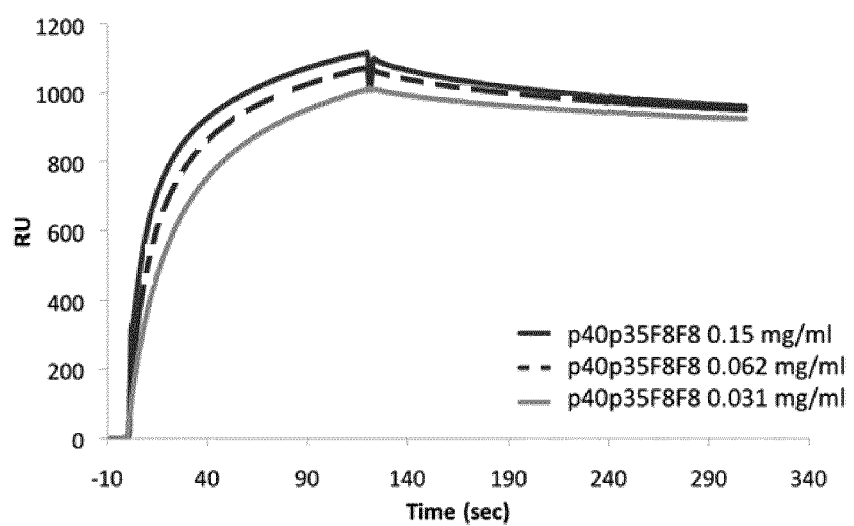
FIG. 4 shows the results of a Biacore analysis of p40p35F8F8 to calculate the apparent KD (binding affinity constant) of the protein to the antigen ED-A. Each line on the graph represents an independent repeat of the p40p35F8F8 protein. The top line indicates a KD of 0.15 mg/ml, the middle line indicates a KD of 0.062 mg/ml, the bottom line indicates a KD of 0.031 mg/ml.

The BIAcore analysis produced a graph (shown in FIG. 4) for the p40p35F8F8 protein which was analysed to deduce the affinity of an antibody for the ED-A antigen. The x axis of each graph corresponds to time and the y axis corresponds to Resonance Units (a measure which indicates the binding affinity of the tested antibody for the antigen coated onto the BIAcore chip).

The ascending part of each graph represents the association phase. The steeper the curve in this part of the graph, the faster the association of the antibody with the antigen. The descending part of each graph represents the dissociation phase of the antibody from the antigen. The flatter the curve in this part of the graph is, the slower the dissociation of the antibody from the antigen.

Example 3

In vivo Targeting Performance: Biodistribution

In order to evaluate in vivo targeting performance, the p40p35F8F8 and (p40p35F8)×2 proteins were radio iodinated with $^{125}$I and chloramine-T, and purified on a PD-10 column. Radio labelled antibody was injected intravenously into four 129 SVE mice bearing subcutaneous F9 tumours. Mice were sacrificed 24 hours after injection. Organs were weighed and radioactivity was counted using a Cobra™γ counter. The radioactivity content of representative organs is expressed as the mean±SE percent of the injected dose per gram tissue The results of this experiment are illustrated in FIG. 7.

The immunocytokine (p40p35F8)×2 did not show any tumour uptake. Both the old format protein and p40p35F8F8 showed nice tumour uptake and similar tumour to blood ratios. However, tumour to organ ratios were superior for the new immunocytokine p40p35F8F8 compared to the old format (6:1 vs. 4:1). As the old format protein and the p40p35F8F8 protein had similar molecular weights, the observed improvement in tumour uptake for the new format could not be explained by, for example, the new format having improved penetration due to being a smaller molecule.

Overall the new IL12 fusion protein p40p35F8F8 shows several advantages over the old format. It is easier to produce and purify since it consists of one single species, which will facilitate production. Furthermore, it shows improved tumour uptake in vivo.

REFERENCES

All documents cited in this specification, including those cited above, are hereby incorporated by reference in their entirety.

1. Savage, P., So, A., Spooner, R. A. & Epenetos, A. A. A recombinant single chain antibody interleukin-2 fusion protein. *Br J Cancer* 67, 304-310 (1993).
2. Schrama, D., Reisfeld, R. A. & Becker, J. C. Antibody targeted drugs as cancer therapeutics. *Nat Rev Drug Discov* 5, 147-159 (2006).
3. Neri, D. & Bicknell, R. Tumour vascular targeting. *Nat Rev Cancer* 5, 436-446 (2005).
4. Dela Cruz, J. S., Huang, T. H., Penichet, M. L. & Morrison, S. L. Antibody-cytokine fusion proteins: innovative weapons in the war against cancer. *Clin Exp Med* 4, 57-64 (2004).
5. Reisfeld, R. A., Becker, J. C. & Gillies, S. D. Immunocytokines: a new approach to immunotherapy of melanoma. *Melanoma Res* 7 Suppl 2, S99-106 (1997).
6. Rodolfo, M. & Colombo, M. P. Interleukin-12 as an adjuvant for cancer immunotherapy. *Methods* 19, 114-120 (1999).
7. Tsung, K., Meko, J. B., Peplinski, G. R., Tsung, Y. L. & Norton, J. A. IL-12 induces T helper 1-directed antitumor response. *J Immunol* 158, 3359-3365 (1997).
8. Brunda, M. J., et al. Antitumor and antimetastatic activity of interleukin 12 against murine tumors. *J Exp Med* 178, 1223-1230 (1993).
9. D'Andrea, A., et al. Production of natural killer cell stimulatory factor (interleukin 12) by peripheral blood mononuclear cells. *J Exp Med* 176, 1387-1398 (1992).
10. Gillessen, S., et al. Mouse interleukin-12 (IL-12) p40 homodimer: a potent IL-12 antagonist. *Eur J Immunol* 25, 200-206 (1995).
11. Ling, P., et al. Human IL-12 p40 homodimer binds to the IL-12 receptor but does not mediate biologic activity. *J Immunol* 154, 116-127 (1995).
12. Carra, G., Gerosa, F. & Trinchieri, G. Biosynthesis and posttranslational regulation of human IL-12. *J Immunol* 164, 4752-4761 (2000).
13. Nastala, C. L., et al. Recombinant IL-12 administration induces tumor regression in association with IFN-gamma production. *J Immunol* 153, 1697-1706 (1994).
14. Magram, J., et al. IL-12-deficient mice are defective in IFN gamma production and type 1 cytokine responses. *Immunity* 4, 471-481 (1996).
15. Murphy, E. E., et al. B7 and interleukin 12 cooperate for proliferation and interferon gamma production by mouse T helper clones that are unresponsive to B7 costimulation. *J Exp Med* 180, 223-231 (1994).
16. Manetti, R., et al. Natural killer cell stimulatory factor (interleukin 12 [IL-12]) induces T helper type 1 (Th1)-specific immune responses and inhibits the development of IL-4-producing Th cells. *J Exp Med* 177, 1199-1204 (1993).
17. Voest, E. E., et al. Inhibition of angiogenesis in vivo by interleukin 12. *J Natl Cancer Inst* 87, 581-586 (1995).
18. Angiolillo, A. L., et al. Human interferon-inducible protein 10 is a potent inhibitor of angiogenesis in vivo. *J Exp Med* 182, 155-162 (1995).
19. Angiolillo, A. L., Sgadari, C. & Tosato, G. A role for the interferon-inducible protein 10 in inhibition of angiogenesis by interleukin-12. *Ann N Y Acad Sci* 795, 158-167 (1996).
20. Atkins, M. B., et al. Phase I evaluation of intravenous recombinant human interleukin 12 in patients with advanced malignancies. *Clin Cancer Res* 3, 409-417 (1997).
21. Gollob, J. A., et al. Phase I trial of twice-weekly intravenous interleukin 12 in patients with metastatic renal cell cancer or malignant melanoma: ability to maintain IFN-gamma induction is associated with clinical response. *Clin Cancer Res* 6, 1678-1692 (2000).
22. Jain, R. K. & Baxter, L. T. Mechanisms of heterogeneous distribution of monoclonal antibodies and other macromolecules in tumors: significance of elevated interstitial pressure. *Cancer Res* 48, 7022-7032 (1988).
23. Folkman, J. Angiogenesis in cancer, vascular, rheumatoid and other disease. *Nat Med* 1, 27-31 (1995).
24. Duda, D. G., et al. Direct in vitro evidence and in vivo analysis of the antiangiogenesis effects of interleukin 12. *Cancer Res* 60, 1111-1116 (2000).
25. Pini, A., et al. Design and use of a phage display library. Human antibodies with subnanomolar affinity against a marker of angiogenesis eluted from a two-dimensional gel. *J Biol Chem* 273, 21769-21776 (1998).
26. Villa, A., et al. A high-affinity human monoclonal antibody specific to the alternatively spliced EDA domain of fibronectin efficiently targets tumor neo-vasculature in vivo. *Int J Cancer* 122, 2405-2413 (2008).
27. Brack, S. S., Silacci, M., Birchler, M. & Neri, D. Tumor-targeting properties of novel antibodies specific to the large isoform of tenascin-C. *Clin Cancer Res* 12, 3200-3208 (2006).
28. Sauer, S., et al. Expression of the oncofetal ED-B containing fibronectin isoform in hematologic tumors enables ED-B targeted 131I-L19SIP radioimmunotherapy in Hodgkin lymphoma patients. *Blood* (2009).
29. Johannsen, M., et al. The tumour-targeting human L19-IL2 immunocytokine: preclinical safety studies, phase I clinical trial in patients with solid tumours and expansion into patients with advanced renal cell carcinoma. *Eur J Cancer* 46, 2926-2935 (2010).
30. Halin, C., et al. Enhancement of the antitumor activity of interleukin-12 by targeted delivery to neovasculature. *Nat Biotechnol* 20, 264-269 (2002).
31. Gafner, V., Trachsel, E. & Neri, D. An engineered antibody-interleukin-12 fusion protein with enhanced tumor vascular targeting properties. *Int J Cancer* 119, 2205-2212 (2006).
32. Hudson, P., Kortt, A. High avidity scFv multimers; diabodies and triabodies. *Journal of Immunological Methods.* Volume 231, Issues 1-2, pages 177-189 (2000).
33. Villa A et al. *Int. J. Cancer.* 2008 Jun. 1; 122 (11): 2405-13.
34. Borsi et al. (1987), J. Cell. Biol., 104, 595-600
35. Holliger and Winter. Diabodies: small bispecific antibody fragments. *Cancer Immunol Immunother* (1997) 45: 128-130.
36. Holliger et al, *Proc. Natl. Acad. Sci. USA* 90 6444-6448, 1993
37. Nettelbeck, D. M; Miller, D. W; Jérôme, V; Zuzarte, M; Watkins, S. J; Hawkins, R. E; Müller, R; and Kontermann, R. E. *Molecular Therapy* (2001) 3, 882-891.
38. Kontermann, R. E., and Muller, R. (1999). Intracellular and cell surface display of single-chain diabodies. *J. Immunol. Methods* 226: 179-188.
39. Kornblihtt et al. (1984), *Nucleic Acids Res.* 12, 5853-5868.
40. Paolella et al. (1988), *Nucleic Acids Res.* 16, 3545-3557.
41. Lohi et al. (1995), *Int. J. Cancer,* 63, 442-449
42. Jacobs et al. (2002), *Hum. Pathol.,* 33, 29-38.
43. Matsumoto et al. (1999), *Jpn. J. Cancer Res.,* 90, 320-325.
44. Oyama et al. (1989), J. Biol. Chem., 264, 10331-10334.
45. Tavian et al. (1994), Int. J. Cancer, 56, 820-825.

What is claimed is:

1. A conjugate comprising interleukin 12 (IL-12) subunit p40 linked to IL-12 subunit p35, wherein the IL-12 subunit p35 is further linked to a single chain diabody comprising a first region comprising VH and VL domains linked to a second region comprising VH and VL domains, wherein the VH and VL domains of the first and second regions comprise complementarity determining regions (CDRs) of an antibody that binds an extracellular matrix component associated with neoplastic growth and/or angiogenesis, and wherein the VH domain of the first region pairs with the VL domain of the second region to form a first antigen binding site and the VH domain of the second region pairs with the VL domain of the first region to form a second antigen binding site.

2. The conjugate according to claim 1, wherein the single chain diabody is linked to the C terminus of the p35 subunit.

3. The conjugate according to claim 1, wherein the p40 subunit has a free N terminus.

4. The conjugate according to claim 1, wherein the single chain diabody binds fibronectin.

5. The conjugate according to claim 4, wherein the single chain diabody binds fibronectin domain ED-A.

6. The conjugate according to claim 5, wherein the first and second antigen binding sites of the single chain diabody comprise the complementarity determining regions (CDRs) of antibody F8 set forth in SEQ ID NOs: 9-14.

7. The conjugate according to claim 5, wherein the single chain diabody has VH and VL domains set forth in SEQ ID NOs: 23 and 24.

8. The conjugate according to claim 7, wherein the single chain diabody comprises the amino acid sequence set forth in SEQ ID NO: 31.

9. The conjugate according to claim 1, which is a single chain fusion protein.

10. The conjugate of claim 1, further comprising a linker between the VH and VL domains of the first region that does not allow pairing between the VH and VL domains of the first region.

11. The conjugate of claim 1, further comprising a linker between the VH and VL domains of the second region that does not allow pairing between the VH and VL domains of the second region.

12. The conjugate of claim 10, further comprising a linker between the VH and VL domains of the second region that does not allow pairing between the VH and VL domains of the second region.

13. The conjugate of claim 1, further comprising a linker between the VL domain of the first region and the VH domain of the second region that allows pairing between the VL domain of the first region and the VH domain of the second region and between the VH domain of the first region and the VL domain of the second region.

14. The conjugate of claim 12, further comprising a linker between the VL domain of the first region and the VH domain of the second region that allows pairing between the VL domain of the first region and the VH domain of the second region and between the VH domain of the first region and the VL domain of the second region.

15. The conjugate of claim 14, the single chain diabody is linked to the C terminus of the p35subunit and the p40 subunit has a free N terminus.

16. The conjugate of claim 15, wherein the single chain diabody binds fibronectin domain ED-A.

17. The conjugate of claim 1, wherein the VH and VL domains of the first region are the same as the VH and VL domains of the second region.

18. The conjugate of claim 1, wherein the VH and VL domains of the first region are different from the VH and VL domains of the second region.

* * * * *

SEQUENCE LISTING

<160> NUMBER OF SEQ ID NOS: 49

<210> SEQ ID NO 1
<211> LENGTH: 3003
<212> TYPE: DNA
<213> ORGANISM: Artificial sequence
<220> FEATURE:
<223> OTHER INFORMATION: Synthetic sequence: P40p35F8F8 nucleotide sequence

<400> SEQUENCE: 1

```
atatgggaac tgaagaaaga tgtttatgtc gtagaattgg attggtatcc ggatgcccct      60
ggagaaatgg tggtcctcac ctgtgacacc cctgaagaag atggtatcac ctggaccttg     120
gaccagagca gtgaggtctt aggctctggc aaaaccctga ccatccaagt caaagagttt     180
ggagatgctg ccagtacac ctgtcacaaa ggaggcgagg ttctaagcca ttcgctcctg      240
ctgcttcaca aaaggaaga tggaatttgg tccactgata ttttaaagga ccagaaagaa     300
cccaaaaata gacctttct aagatgcgag gccaagaatt attctggacg tttcacctgc     360
tggtggctga cgacaatcag tactgatttg acattcagtg tcaaaagcag cagaggctct     420
tctgaccccc aaggggtgac gtgcggagct gctacactct ctgcagagag agtcagaggg    480
gacaacaagg agtatgagta ctcagtggag tgccaggagg acagtgcctg cccagctgct    540
gaggagagtc tgcccattga ggtcatggtg gatgccgttc acaagctcaa gtatgaaaac    600
tacaccagca gcttcttcat cagggacatc atcaaacctg acccacccaa gaacttgcag    660
ctgaagccat taaagaattc tcggcaggtg gaggtcagct gggagtaccc tgacacctgg    720
agtactccac attcctactt ctccctgaca ttctgcgttc aggtccaggg caagagcaag    780
agagaaaaga agatagagt cttcacggac aagacctcag ccacggtcat ctgccgcaaa    840
aatgccagca ttagcgtgcg ggcccaggac cgctactata gctcatcttg gagcgaatgg    900
gcatctgtgc cctgcagtgg tggaggcggt tcaggcggag gtggctctgg cggtggcgga    960
tcgagaaacc tccccgtggc cactccagac ccaggaatgt tcccatgcct tcaccactcc   1020
caaaacctgc tgagggccgt cagcaacatg ctccagaagg ccagacaaac tctagaattt   1080
taccccttgca cttctgaaga gattgatcat gaagatatca caaagataa aaccagcaca   1140
gtggaggcct gtttaccatt ggaattaacc aagaatgaga gttgcctaaa ttccagagag   1200
acctcttca taactaatgg gagttgcctg gcctccagaa agacctcttt tatgatggcc   1260
ctgtgcctta gtagtattta tgaagacttg aagatgtacc aggtggagtt caagaccatg   1320
aatgcaaagc ttctgatgga tcctaagagg cagatctttc tagatcaaaa catgctggca   1380
gttattgatg agctgatgca ggccctgaat ttcaacagtg agactgtgcc acaaaaatcc   1440
tcccttgaag aaccggattt ttataaaact aaaatcaagc tctgcatact tcttcatgct   1500
ttcagaattc gggcagtgac tattgataga gtgatgagct atctgaatgc ttccggtagc   1560
gctgatggag gtgaggtgca gctgttggag tctgggggag gcttggtaca gcctgggggg   1620
tccctgagac tctcctgtgc agcctctgga ttcacctta gcctgtttac gatgagctgg   1680
gtccgccagg ctccagggaa ggggctggag tgggtctcag ctattagtgg tagtggtggt   1740
agcacatact acgcagactc cgtgaagggc cggttcacca tctccagaga caattccaag   1800
aacacgctgt atctgcaaat gaacagcctg agagccgagg acacggccgt atattactgt   1860
gcgaaaagta tcatttgta tctttttgac tactgggggcc agggaaccct ggtcaccgtc   1920
tcgagtggcg gtagcggagg ggaaattgtg ttgacgcagt ctccaggcac cctgtctttg   1980
```

-continued

```
tctccagggg aaagagccac cctctcctgc agggccagtc agagtgttag catgccgttt    2040
ttagcctggt accagcagaa acctggccag gctcccaggc tcctcatcta tggtgcatcc    2100
agcagggcca ctggcatccc agacaggttc agtggcagtg ggtctgggac agacttcact    2160
ctcaccatca gcagactgga gcctgaagat tttgcagtgt attactgtca gcagatgcgt    2220
ggtcggccgc cgacgttcgg ccaagggacc aaggtggaaa tcaaatcttc ctcatccgga    2280
agtagctctt ccggctcatc gtccagcggc gaggtgcagc tgttggagtc tggggggaggc    2340 ttggtacagc ctggggggtc cctgagactc tcctgtgcag cctctggatt cacctttagc    2400
ctgtttacga tgagctgggt ccgccaggct ccagggaagg ggctgagtg ggtctcagct     2460 attagtggta gtggtggtag cacatactac gcagactccg tgaagggccg gttcaccatc    2520
tccagagaca attccaagaa cacgctgtat ctgcaaatga acagcctgag agccgaggac    2580
acggccgtat attactgtgc gaaaagtact catttgtatc tttttgacta ctggggccag    2640
ggaaccctgg tcaccgtctc gagtggcggt agcggagggg aaattgtgtt gacgcagtct    2700
ccaggcaccc tgtctttgtc tccagggaa agagccaccc tctcctgcag ggccagtcag    2760
agtgttagca tgccgttttt agcctggtac cagcagaaac ctggccaggc tcccaggctc    2820
ctcatctatg gtgcatccag cagggccact ggcatcccag acaggttcag tggcagtggg    2880
tctgggacag acttcactct caccatcagc agactggagc ctgaagattt tgcagtgtat    2940
tactgtcagc agatgcgtgg tcggccgccg acgttcggcc aagggaccaa ggtggaaatc    3000
aaa                                                                  3003
```

<210> SEQ ID NO 2
<211> LENGTH: 9
<212> TYPE: DNA
<213> ORGANISM: Homo sapiens

<400> SEQUENCE: 2 ctgtttacg                                                               9

<210> SEQ ID NO 3
<211> LENGTH: 18
<212> TYPE: DNA
<213> ORGANISM: Homo sapiens

<400> SEQUENCE: 3
agtggtagtg gtggtagc                                                    18

<210> SEQ ID NO 4
<211> LENGTH: 18
<212> TYPE: DNA
<213> ORGANISM: Homo sapiens

<400> SEQUENCE: 4
agtactcatt tgtatctt                                                    18

<210> SEQ ID NO 5
<211> LENGTH: 9
<212> TYPE: DNA
<213> ORGANISM: Homo sapiens

<400> SEQUENCE: 5 atgccgttt                                                               9

<210> SEQ ID NO 6
<211> LENGTH: 21

```
<212> TYPE: DNA
<213> ORGANISM: Homo sapiens

<400> SEQUENCE: 6
ggtgcatcca gcagggccac t                                              21

<210> SEQ ID NO 7
<211> LENGTH: 18
<212> TYPE: DNA
<213> ORGANISM: Homo sapiens

<400> SEQUENCE: 7
atgcgtggtc ggccgccg                                                  18

<210> SEQ ID NO 8
<211> LENGTH: 1001
<212> TYPE: PRT
<213> ORGANISM: Artificial sequence
<220> FEATURE:
<223> OTHER INFORMATION: Synthetic sequence: P40p35F8F8 amino acid
      sequence

<400> SEQUENCE: 8
```

| | | | | | | | | | | | | | | | |
|---|---|---|---|---|---|---|---|---|---|---|---|---|---|---|---|
| Ile | Trp | Glu | Leu | Lys | Lys | Asp | Val | Tyr | Val | Glu | Leu | Asp | Trp | Tyr | |
| 1 | | | | 5 | | | | | 10 | | | | | 15 | |
| Pro | Asp | Ala | Pro | Gly | Glu | Met | Val | Val | Leu | Thr | Cys | Asp | Thr | Pro | Glu |
| | | | 20 | | | | | 25 | | | | | 30 | | |
| Glu | Asp | Gly | Ile | Thr | Trp | Thr | Leu | Asp | Gln | Ser | Ser | Glu | Val | Leu | Gly |
| | | | 35 | | | | | 40 | | | | | 45 | | |
| Ser | Gly | Lys | Thr | Leu | Thr | Ile | Gln | Val | Lys | Glu | Phe | Gly | Asp | Ala | Gly |
| | 50 | | | | | 55 | | | | | 60 | | | | |
| Gln | Tyr | Thr | Cys | His | Lys | Gly | Gly | Glu | Val | Leu | Ser | His | Ser | Leu | Leu |
| 65 | | | | | 70 | | | | | 75 | | | | | 80 |
| Leu | Leu | His | Lys | Lys | Glu | Asp | Gly | Ile | Trp | Ser | Thr | Asp | Ile | Leu | Lys |
| | | | | 85 | | | | | 90 | | | | | 95 | |
| Asp | Gln | Lys | Glu | Pro | Lys | Asn | Lys | Thr | Phe | Leu | Arg | Cys | Glu | Ala | Lys |
| | | | 100 | | | | | 105 | | | | | 110 | | |
| Asn | Tyr | Ser | Gly | Arg | Phe | Thr | Cys | Trp | Trp | Leu | Thr | Thr | Ile | Ser | Thr |
| | | | 115 | | | | | 120 | | | | | 125 | | |
| Asp | Leu | Thr | Phe | Ser | Val | Lys | Ser | Ser | Arg | Gly | Ser | Ser | Asp | Pro | Gln |
| | 130 | | | | | 135 | | | | | 140 | | | | |
| Gly | Val | Thr | Cys | Gly | Ala | Ala | Thr | Leu | Ser | Ala | Glu | Arg | Val | Arg | Gly |
| 145 | | | | | 150 | | | | | 155 | | | | | 160 |
| Asp | Asn | Lys | Glu | Tyr | Glu | Tyr | Ser | Val | Glu | Cys | Gln | Glu | Asp | Ser | Ala |
| | | | | 165 | | | | | 170 | | | | | 175 | |
| Cys | Pro | Ala | Ala | Glu | Glu | Ser | Leu | Pro | Ile | Glu | Val | Met | Val | Asp | Ala |
| | | | 180 | | | | | 185 | | | | | 190 | | |
| Val | His | Lys | Leu | Lys | Tyr | Glu | Asn | Tyr | Thr | Ser | Ser | Phe | Phe | Ile | Arg |
| | | | 195 | | | | | 200 | | | | | 205 | | |
| Asp | Ile | Ile | Lys | Pro | Asp | Pro | Pro | Lys | Asn | Leu | Gln | Leu | Lys | Pro | Leu |
| | 210 | | | | | 215 | | | | | 220 | | | | |
| Lys | Asn | Ser | Arg | Gln | Val | Glu | Val | Ser | Trp | Glu | Tyr | Pro | Asp | Thr | Trp |
| 225 | | | | | 230 | | | | | 235 | | | | | 240 |
| Ser | Thr | Pro | His | Ser | Tyr | Phe | Ser | Leu | Thr | Phe | Cys | Val | Gln | Val | Gln |
| | | | | 245 | | | | | 250 | | | | | 255 | |
| Gly | Lys | Ser | Lys | Arg | Glu | Lys | Lys | Asp | Arg | Val | Phe | Thr | Asp | Lys | Thr |
| | | | 260 | | | | | 265 | | | | | 270 | | |

```
Ser Ala Thr Val Ile Cys Arg Lys Asn Ala Ser Ile Ser Val Arg Ala
            275                 280                 285
Gln Asp Arg Tyr Tyr Ser Ser Trp Ser Glu Trp Ala Ser Val Pro
    290                 295                 300
Cys Ser Gly Gly Gly Ser Gly Gly Gly Ser Gly Gly Gly Gly
305                 310                 315                 320
Ser Arg Asn Leu Pro Val Ala Thr Pro Asp Pro Gly Met Phe Pro Cys
                325                 330                 335
Leu His His Ser Gln Asn Leu Leu Arg Ala Val Ser Asn Met Leu Gln
            340                 345                 350
Lys Ala Arg Gln Thr Leu Glu Phe Tyr Pro Cys Thr Ser Glu Glu Ile
        355                 360                 365
Asp His Glu Asp Ile Thr Lys Asp Lys Thr Ser Thr Val Glu Ala Cys
370                 375                 380
Leu Pro Leu Glu Leu Thr Lys Asn Glu Ser Cys Leu Asn Ser Arg Glu
385                 390                 395                 400
Thr Ser Phe Ile Thr Asn Gly Ser Cys Leu Ala Ser Arg Lys Thr Ser
                405                 410                 415
Phe Met Met Ala Leu Cys Leu Ser Ser Ile Tyr Glu Asp Leu Lys Met
                420                 425                 430
Tyr Gln Val Glu Phe Lys Thr Met Asn Ala Lys Leu Leu Met Asp Pro
        435                 440                 445
Lys Arg Gln Ile Phe Leu Asp Gln Asn Met Leu Ala Val Ile Asp Glu
    450                 455                 460
Leu Met Gln Ala Leu Asn Phe Asn Ser Glu Thr Val Pro Gln Lys Ser
465                 470                 475                 480
Ser Leu Glu Glu Pro Asp Phe Tyr Lys Thr Lys Ile Lys Leu Cys Ile
                485                 490                 495
Leu Leu His Ala Phe Arg Ile Arg Ala Val Thr Ile Asp Arg Val Met
                500                 505                 510
Ser Tyr Leu Asn Ala Ser Gly Ser Ala Asp Gly Gly Glu Val Gln Leu
            515                 520                 525
Leu Glu Ser Gly Gly Gly Leu Val Gln Pro Gly Gly Ser Leu Arg Leu
530                 535                 540
Ser Cys Ala Ala Ser Gly Phe Thr Phe Ser Leu Phe Thr Met Ser Trp
545                 550                 555                 560
Val Arg Gln Ala Pro Gly Lys Gly Leu Glu Trp Val Ser Ala Ile Ser
                565                 570                 575
Gly Ser Gly Gly Ser Thr Tyr Tyr Ala Asp Ser Val Lys Gly Arg Phe
                580                 585                 590
Thr Ile Ser Arg Asp Asn Ser Lys Asn Thr Leu Tyr Leu Gln Met Asn
            595                 600                 605
Ser Leu Arg Ala Glu Asp Thr Ala Val Tyr Tyr Cys Ala Lys Ser Thr
        610                 615                 620
His Leu Tyr Leu Phe Asp Tyr Trp Gly Gln Gly Thr Leu Val Thr Val
625                 630                 635                 640
Ser Ser Gly Gly Ser Gly Gly Glu Ile Val Leu Thr Gln Ser Pro Gly
                645                 650                 655
Thr Leu Ser Leu Ser Pro Gly Glu Arg Ala Thr Leu Ser Cys Arg Ala
            660                 665                 670
Ser Gln Ser Val Ser Met Pro Phe Leu Ala Trp Tyr Gln Gln Lys Pro
        675                 680                 685
Gly Gln Ala Pro Arg Leu Leu Ile Tyr Gly Ala Ser Ser Arg Ala Thr
```

```
                690                 695                 700
Gly Ile Pro Asp Arg Phe Ser Gly Ser Gly Thr Asp Phe Thr
705                 710                 715                 720

Leu Thr Ile Ser Arg Leu Glu Pro Glu Asp Phe Ala Val Tyr Tyr Cys
                725                 730                 735

Gln Gln Met Arg Gly Arg Pro Pro Thr Phe Gly Gln Gly Thr Lys Val
            740                 745                 750

Glu Ile Lys Ser Ser Ser Gly Ser Ser Ser Gly Ser Ser Ser
            755                 760                 765

Ser Gly Glu Val Gln Leu Leu Glu Ser Gly Gly Gly Leu Val Gln Pro
        770                 775                 780

Gly Gly Ser Leu Arg Leu Ser Cys Ala Ala Ser Gly Phe Thr Phe Ser
785                 790                 795                 800

Leu Phe Thr Met Ser Trp Val Arg Gln Ala Pro Gly Lys Gly Leu Glu
                805                 810                 815

Trp Val Ser Ala Ile Ser Gly Ser Gly Gly Ser Thr Tyr Tyr Ala Asp
                820                 825                 830

Ser Val Lys Gly Arg Phe Thr Ile Ser Arg Asp Asn Ser Lys Asn Thr
            835                 840                 845

Leu Tyr Leu Gln Met Asn Ser Leu Arg Ala Glu Asp Thr Ala Val Tyr
        850                 855                 860

Tyr Cys Ala Lys Ser Thr His Leu Tyr Leu Phe Asp Tyr Trp Gly Gln
865                 870                 875                 880

Gly Thr Leu Val Thr Val Ser Ser Gly Gly Ser Gly Gly Glu Ile Val
                885                 890                 895

Leu Thr Gln Ser Pro Gly Thr Leu Ser Leu Ser Pro Gly Glu Arg Ala
            900                 905                 910

Thr Leu Ser Cys Arg Ala Ser Gln Ser Val Ser Met Pro Phe Leu Ala
            915                 920                 925

Trp Tyr Gln Gln Lys Pro Gly Gln Ala Pro Arg Leu Leu Ile Tyr Gly
            930                 935                 940

Ala Ser Ser Arg Ala Thr Gly Ile Pro Asp Arg Phe Ser Gly Ser Gly
945                 950                 955                 960

Ser Gly Thr Asp Phe Thr Leu Thr Ile Ser Arg Leu Glu Pro Glu Asp
                965                 970                 975

Phe Ala Val Tyr Tyr Cys Gln Gln Met Arg Gly Arg Pro Pro Thr Phe
                980                 985                 990

Gly Gln Gly Thr Lys Val Glu Ile Lys
            995                 1000
```

<210> SEQ ID NO 9
<211> LENGTH: 3
<212> TYPE: PRT
<213> ORGANISM: Homo sapiens

<400> SEQUENCE: 9

Leu Phe Thr
1

<210> SEQ ID NO 10
<211> LENGTH: 5
<212> TYPE: PRT
<213> ORGANISM: Homo sapiens

<400> SEQUENCE: 10

Ala Ile Ser Gly Ser

```
<210> SEQ ID NO 11
<211> LENGTH: 6
<212> TYPE: PRT
<213> ORGANISM: Homo sapiens

<400> SEQUENCE: 11

Ser Thr His Leu Tyr Leu
1               5

<210> SEQ ID NO 12
<211> LENGTH: 3
<212> TYPE: PRT
<213> ORGANISM: Homo sapiens

<400> SEQUENCE: 12

Met Pro Phe
1

<210> SEQ ID NO 13
<211> LENGTH: 7
<212> TYPE: PRT
<213> ORGANISM: Homo sapiens

<400> SEQUENCE: 13

Gly Ala Ser Ser Arg Ala Thr
1               5

<210> SEQ ID NO 14
<211> LENGTH: 6
<212> TYPE: PRT
<213> ORGANISM: Homo sapiens

<400> SEQUENCE: 14

Met Arg Gly Arg Pro Pro
1               5

<210> SEQ ID NO 15
<211> LENGTH: 118
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

```
<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 17
<211> LENGTH: 306
<212> TYPE: PRT
<213> ORGANISM: Homo sapiens

<400> SEQUENCE: 17

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
```

```
                225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
            290                 295                 300

Cys Ser
305

<210> SEQ ID NO 18
<211> LENGTH: 197
<212> TYPE: PRT
<213> ORGANISM: Homo sapiens

<400> SEQUENCE: 18

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 19
<211> LENGTH: 15
<212> TYPE: PRT
<213> ORGANISM: Artificial sequence
<220> FEATURE:
<223> OTHER INFORMATION: Synthetic sequence: Peptide linker sequence

<400> SEQUENCE: 19

Gly Gly Gly Gly Ser Gly Gly Gly Ser Gly Gly Gly Gly Ser
1               5                   10                  15

<210> SEQ ID NO 20
```

```
<211> LENGTH: 6
<212> TYPE: PRT
<213> ORGANISM: Artificial sequence
<220> FEATURE:
<223> OTHER INFORMATION: Synthetic sequence: Peptide linker sequence

<400> SEQUENCE: 20

Gly Ser Ala Asp Gly Gly
1               5

<210> SEQ ID NO 21
<211> LENGTH: 5
<212> TYPE: PRT
<213> ORGANISM: Artificial sequence
<220> FEATURE:
<223> OTHER INFORMATION: Synthetic sequence: Peptide linker sequence

<400> SEQUENCE: 21

Gly Gly Ser Gly Gly
1               5

<210> SEQ ID NO 22
<211> LENGTH: 15
<212> TYPE: PRT
<213> ORGANISM: Artificial sequence
<220> FEATURE:
<223> OTHER INFORMATION: Synthetic sequence: Peptide linker sequence

<400> SEQUENCE: 22

Ser Ser Ser Ser Gly Ser Ser Ser Gly Ser Ser Ser Ser Ser Gly
1               5                   10                  15

<210> SEQ ID NO 23
<211> LENGTH: 354
<212> TYPE: DNA
<213> ORGANISM: Homo sapiens

<400> SEQUENCE: 23
gaggtgcagc tgttggagtc tgggggaggc ttggtacagc ctggggggtc cctgagactc      60
tcctgtgcag cctctggatt cacctttagc ctgtttacga tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagtact     300
catttgtatc ttttgactac tggggccag ggaaccctgg tcaccgtctc gagt            354

<210> SEQ ID NO 24
<211> LENGTH: 324
<212> TYPE: DNA
<213> ORGANISM: Homo sapiens

<400> SEQUENCE: 24
gaaattgtgt tgacgcagtc tccaggcacc ctgtctttgt ctccagggga aagagccacc      60
ctctcctgca gggccagtca gagtgttagc atgccgtttt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg tcggccgcc gacgttcggc      300 caagggacca aggtggaaat caaa                                            324

<210> SEQ ID NO 25
```

```
<211> LENGTH: 918
<212> TYPE: DNA
<213> ORGANISM: Homo sapiens

<400> SEQUENCE: 25
atatgggaac tgaagaaaga tgtttatgtc gtagaattgg attggtatcc ggatgcccct       60
ggagaaatgg tggtcctcac ctgtgacacc cctgaagaag atggtatcac ctggaccttg      120
gaccagagca gtgaggtctt aggctctggc aaaaccctga ccatccaagt caaagagttt      180
ggagatgctg ccagtacac ctgtcacaaa ggaggcgagg ttctaagcca ttcgctcctg       240
ctgcttcaca aaaaggaaga tggaatttgg tccactgata ttttaaagga ccagaaagaa      300
cccaaaaata gacctttct aagatgcgag gccaagaatt attctggacg tttcacctgc       360
tggtggctga cgacaatcag tactgatttg acattcagtg tcaaaagcag cagaggctct      420 tctgacccccc aaggggtgac gtgcggagct gctacactct ctgcagagag agtcagaggg    480
gacaacaagg agtatgagta ctcagtggag tgccaggagg acagtgcctg cccagctgct      540
gaggagagtc tgcccattga ggtcatggtg gatgccgttc acaagctcaa gtatgaaaac      600
tacaccagca gcttcttcat cagggacatc atcaaacctg acccacccaa gaacttgcag      660
ctgaagccat taaagaattc tcggcaggtg gaggtcagct gggagtaccc tgacacctgg      720
agtactccac attcctactt ctccctgaca ttctgcgttc aggtccaggg caagagcaag      780
agagaaaaga aagatagagt cttcacggac aagacctcag ccacggtcat ctgccgcaaa      840
aatgccagca ttagcgtgcg ggcccaggac cgctactata gctcatcttg gagcgaatgg      900
gcatctgtgc cctgcagt                                                    918

<210> SEQ ID NO 26
<211> LENGTH: 591
<212> TYPE: DNA
<213> ORGANISM: Homo sapiens

<400> SEQUENCE: 26
agaaacctcc ccgtggccac tccagaccca ggaatgttcc catgccttca ccactcccaa       60
aacctgctga gggccgtcag caacatgctc cagaaggcca gacaaactct agaattttac      120
ccttgcactt ctgaagagat tgatcatgaa gatatcacaa aagataaaac cagcacagtg      180
gaggcctgtt taccattgga attaaccaag aatgagagtt gcctaaattc cagagagacc      240
tctttcataa ctaatgggag ttgcctggcc tccagaaaga cctcttttat gatggccctg      300
tgccttagta gtatttatga agacttgaag atgtaccagg tggagttcaa gaccatgaat      360
gcaaagcttc tgatggatcc taagaggcag atctttctag atcaaaacat gctggcagtt      420
attgatgagc tgatgcaggc cctgaatttc aacagtgaga ctgtgccaca aaaatcctcc      480
cttgaagaac cggattttta taaaactaaa atcaagctct gcatacttct tcatgctttc      540
agaattcggg cagtgactat tgatagagtg atgagctatc tgaatgcttc c              591

<210> SEQ ID NO 27
<211> LENGTH: 45
<212> TYPE: DNA
<213> ORGANISM: Artificial sequence
<220> FEATURE:
<223> OTHER INFORMATION: Synthetic sequence: linker sequence

<400> SEQUENCE: 27
ggtggaggcg gttcaggcgg aggtggctct ggcggtggcg gatcg                       45
```

```
<210> SEQ ID NO 28
<211> LENGTH: 18
<212> TYPE: DNA
<213> ORGANISM: Artificial sequence
<220> FEATURE:
<223> OTHER INFORMATION: Synthetic sequence: linker sequence

<400> SEQUENCE: 28
ggtagcgctg atggaggt                                                   18

<210> SEQ ID NO 29
<211> LENGTH: 15
<212> TYPE: DNA
<213> ORGANISM: Artificial sequence
<220> FEATURE:
<223> OTHER INFORMATION: Synthetic sequence: linker sequence

<400> SEQUENCE: 29
ggcggtagcg gaggg                                                      15

<210> SEQ ID NO 30
<211> LENGTH: 45
<212> TYPE: DNA
<213> ORGANISM: Artificial sequence
<220> FEATURE:
<223> OTHER INFORMATION: Synthetic sequence: linker sequence

<400> SEQUENCE: 30
tcttcctcat ccggaagtag ctcttccggc tcatcgtcca gcggc                     45

<210> SEQ ID NO 31
<211> LENGTH: 1431
<212> TYPE: DNA
<213> ORGANISM: Artificial sequence
<220> FEATURE:
<223> OTHER INFORMATION: Synthetic sequence: F8 single chain diabody
      sequence

<400> SEQUENCE: 31
gaggtgcagc tgttggagtc tgggggaggc ttggtacagc ctggggggtc cctgagactc     60
tcctgtgcag cctctggatt cacctttagc ctgtttacga tgagctgggt ccgccaggct    120
ccagggaagg ggctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc ttttgactac tggggccag ggaaccctgg tcaccgtctc gagtggcggt    360
agcggagggg aaattgtgtt gacgcagtct ccaggcaccc tgtctttgtc tccaggggaa    420
agagccaccc tctcctgcag ggccagtcag agtgttagca tgccgtttttt agcctggtac    480 cagcagaaac tggccaggc tcccaggctc ctcatctatg gtgcatccag cagggccact    540
ggcatcccag acaggttcag tggcagtggg tctgggacag acttcactct caccatcagc    600
agactggagc ctgaagattt tgcagtgtat tactgtcagc agatgcgtgg tcggccgccg    660
acgttcggcc aagggaccaa ggtggaaatc aaatcttcct catccggaag tagctcttcc    720
ggctcatcgt ccagcggcga ggtgcagctg ttggagtctg ggggaggctt ggtacagcct    780
ggggggtccc tgagactctc ctgtgcagcc tctggattca cctttagcct gtttacgatg    840
agctgggtcc gccaggctcc agggaagggg ctggagtggg tctcagctat tagtggtagt    900
ggtggtagca catactacgc agactccgtg aagggccggt tcaccatctc cagagacaat    960
tccaagaaca cgctgtatct gcaaatgaac agcctgagag ccgaggacac ggccgtatat   1020
```

```
tactgtgcga aaagtactca tttgtatctt tttgactact ggggccaggg aaccctggtc   1080
accgtctcga gtggcggtag cggagggggaa attgtgttga cgcagtctcc aggcaccctg   1140
tctttgtctc caggggaaag agccaccctc tcctgcaggg ccagtcagag tgttagcatg   1200
ccgtttttag cctggtacca gcagaaacct ggccaggctc ccaggctcct catctatggt   1260
gcatccagca gggccactgg catcccagac aggttcagtg gcagtgggtc tgggacagac   1320
ttcactctca ccatcagcag actggagcct gaagattttg cagtgtatta ctgtcagcag   1380
atgcgtggtc ggccgccgac gttcggccaa gggaccaagg tggaaatcaa a           1431
```

<210> SEQ ID NO 32
<211> LENGTH: 680
<212> TYPE: PRT
<213> ORGANISM: Artificial sequence
<220> FEATURE:
<223> OTHER INFORMATION: Synthetic sequence: F8 single chain diabody
      sequence

<400> SEQUENCE: 32

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Ser Ala Asp Gly Gly Glu Val Gln Leu Leu
        195                 200                 205

Glu Ser Gly Gly Gly Leu Val Gln Pro Gly Gly Ser Leu Arg Leu Ser
    210                 215                 220

Cys Ala Ala Ser Gly Phe Thr Phe Ser Leu Phe Thr Met Ser Trp Val
225                 230                 235                 240

Arg Gln Ala Pro Gly Lys Gly Leu Glu Trp Val Ser Ala Ile Ser Gly
                245                 250                 255

Ser Gly Gly Ser Thr Tyr Tyr Ala Asp Ser Val Lys Gly Arg Phe Thr
            260                 265                 270

Ile Ser Arg Asp Asn Ser Lys Asn Thr Leu Tyr Leu Gln Met Asn Ser
        275                 280                 285
```

```
Leu Arg Ala Glu Asp Thr Ala Val Tyr Tyr Cys Ala Lys Ser Thr His
        290                 295                 300

Leu Tyr Leu Phe Asp Tyr Trp Gly Gln Gly Thr Leu Val Thr Val Ser
305                 310                 315                 320

Ser Gly Gly Ser Gly Gly Glu Ile Val Leu Thr Gln Ser Pro Gly Thr
                325                 330                 335

Leu Ser Leu Ser Pro Gly Glu Arg Ala Thr Leu Ser Cys Arg Ala Ser
            340                 345                 350

Gln Ser Val Ser Met Pro Phe Leu Ala Trp Tyr Gln Gln Lys Pro Gly
        355                 360                 365

Gln Ala Pro Arg Leu Leu Ile Tyr Gly Ala Ser Ser Arg Ala Thr Gly
    370                 375                 380

Ile Pro Asp Arg Phe Ser Gly Ser Gly Ser Gly Thr Asp Phe Thr Leu
385                 390                 395                 400

Thr Ile Ser Arg Leu Glu Pro Glu Asp Phe Ala Val Tyr Tyr Cys Gln
                405                 410                 415

Gln Met Arg Gly Arg Pro Pro Thr Phe Gly Gln Gly Thr Lys Val Glu
            420                 425                 430

Ile Lys Ser Ser Ser Gly Ser Ser Ser Gly Ser Ser Ser Ser
        435                 440                 445

Gly Glu Val Gln Leu Leu Glu Ser Gly Gly Gly Leu Val Gln Pro Gly
    450                 455                 460

Gly Ser Leu Arg Leu Ser Cys Ala Ala Ser Gly Phe Thr Phe Ser Leu
465                 470                 475                 480

Phe Thr Met Ser Trp Val Arg Gln Ala Pro Gly Lys Gly Leu Glu Trp
                485                 490                 495

Val Ser Ala Ile Ser Gly Ser Gly Gly Ser Thr Tyr Tyr Ala Asp Ser
            500                 505                 510

Val Lys Gly Arg Phe Thr Ile Ser Arg Asp Asn Ser Lys Asn Thr Leu
        515                 520                 525

Tyr Leu Gln Met Asn Ser Leu Arg Ala Glu Asp Thr Ala Val Tyr Tyr
    530                 535                 540

Cys Ala Lys Ser Thr His Leu Tyr Leu Phe Asp Tyr Trp Gly Gln Gly
545                 550                 555                 560

Thr Leu Val Thr Val Ser Ser Gly Gly Ser Gly Gly Glu Ile Val Leu
                565                 570                 575

Thr Gln Ser Pro Gly Thr Leu Ser Leu Ser Pro Gly Glu Arg Ala Thr
            580                 585                 590

Leu Ser Cys Arg Ala Ser Gln Ser Val Ser Met Pro Phe Leu Ala Trp
        595                 600                 605

Tyr Gln Gln Lys Pro Gly Gln Ala Pro Arg Leu Leu Ile Tyr Gly Ala
    610                 615                 620

Ser Ser Arg Ala Thr Gly Ile Pro Asp Arg Phe Ser Gly Ser Gly Ser
625                 630                 635                 640

Gly Thr Asp Phe Thr Leu Thr Ile Ser Arg Leu Glu Pro Glu Asp Phe
                645                 650                 655

Ala Val Tyr Tyr Cys Gln Gln Met Arg Gly Arg Pro Pro Thr Phe Gly
            660                 665                 670

Gln Gly Thr Lys Val Glu Ile Lys
        675                 680

<210> SEQ ID NO 33
<211> LENGTH: 116
```

```
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 34
<211> LENGTH: 108
<212> TYPE: PRT
<213> ORGANISM: Homo sapiens

<400> SEQUENCE: 34

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 35
<211> LENGTH: 5
<212> TYPE: PRT
<213> ORGANISM: Homo sapiens

<400> SEQUENCE: 35

Ser Phe Ser Met Ser
 1               5

<210> SEQ ID NO 36
<211> LENGTH: 16
<212> TYPE: PRT
<213> ORGANISM: Homo sapiens

<400> SEQUENCE: 36

Ser Ile Ser Gly Ser Ser Gly Thr Thr Tyr Tyr Ala Asp Ser Val Lys
 1               5                  10                  15
```

<210> SEQ ID NO 37
<211> LENGTH: 7
<212> TYPE: PRT
<213> ORGANISM: Homo sapiens

<400> SEQUENCE: 37

Pro Phe Pro Tyr Phe Asp Tyr
1               5

<210> SEQ ID NO 38
<211> LENGTH: 12
<212> TYPE: PRT
<213> ORGANISM: Homo sapiens

<400> SEQUENCE: 38

Arg Ala Ser Gln Ser Val Ser Ser Ser Phe Leu Ala
1               5                   10

<210> SEQ ID NO 39
<211> LENGTH: 7
<212> TYPE: PRT
<213> ORGANISM: Homo sapiens

<400> SEQUENCE: 39

Tyr Ala Ser Ser Arg Ala Thr
1               5

<210> SEQ ID NO 40
<211> LENGTH: 9
<212> TYPE: PRT
<213> ORGANISM: Homo sapiens

<400> SEQUENCE: 40

Gln Gln Thr Gly Arg Ile Pro Pro Thr
1               5

<210> SEQ ID NO 41
<211> LENGTH: 236
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ser Ser Ile Ser Gly Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Gly Gly Ser Gly Gly Ala Ser
        115                 120                 125

Glu Ile Val Leu Thr Gln Ser Pro Gly Thr Leu Ser Leu Ser Pro Gly
        130                 135                 140

```
Glu Arg Ala Thr Leu Ser Cys Arg Ala Ser Gln Ser Val Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys
225                 230                 235

<210> SEQ ID NO 42
<211> LENGTH: 116
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 43
<211> LENGTH: 108
<212> TYPE: PRT
<213> ORGANISM: Homo sapiens

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu
            100                 105
```

```
<210> SEQ ID NO 44
<211> LENGTH: 5
<212> TYPE: PRT
<213> ORGANISM: Homo sapiens

<400> SEQUENCE: 44

Arg Tyr Gly Met Ser
1               5

<210> SEQ ID NO 45
<211> LENGTH: 17
<212> TYPE: PRT
<213> ORGANISM: Homo sapiens

<400> SEQUENCE: 45

Ala Ile Ser Gly Ser Gly Gly Ser Thr Tyr Tyr Ala Asp Ser Val Lys
1               5                   10                  15

Gly

<210> SEQ ID NO 46
<211> LENGTH: 7
<212> TYPE: PRT
<213> ORGANISM: Homo sapiens

<400> SEQUENCE: 46

Ala His Asn Ala Phe Asp Tyr
1               5

<210> SEQ ID NO 47
<211> LENGTH: 11
<212> TYPE: PRT
<213> ORGANISM: Homo sapiens

<400> SEQUENCE: 47

Gln Gly Asp Ser Leu Arg Ser Tyr Tyr Ala Ser
1               5                   10

<210> SEQ ID NO 48
<211> LENGTH: 7
<212> TYPE: PRT
<213> ORGANISM: Homo sapiens

<400> SEQUENCE: 48

Gly Lys Asn Asn Arg Pro Ser
1               5

<210> SEQ ID NO 49
<211> LENGTH: 11
<212> TYPE: PRT
<213> ORGANISM: Homo sapiens

<400> SEQUENCE: 49

Asn Ser Ser Val Tyr Thr Met Pro Pro Val Val
1               5                   10
```